(12) United States Patent
Fischer

(10) Patent No.: US 11,083,513 B2
(45) Date of Patent: Aug. 10, 2021

(54) ABLATION CATHETER DEVICE WITH ELECTRODES FOR DETECTING AN ELECTRIC RESPONSE OF BIOLOGICAL MATERIAL

(71) Applicant: AFREEZE GMBH, Innsbruck (AT)

(72) Inventor: Gerald Fischer, Völs (AT)

(73) Assignee: Afreeze GmbH, Innsbruck (AT)

( * ) Notice: Subject to any disclaimer, the term of this patent is extended or adjusted under 35 U.S.C. 154(b) by 716 days.

(21) Appl. No.: 15/743,219

(22) PCT Filed: Jul. 7, 2016

(86) PCT No.: PCT/EP2016/066107
§ 371 (c)(1),
(2) Date: Jan. 9, 2018

(87) PCT Pub. No.: WO2017/009165
PCT Pub. Date: Jan. 19, 2017

(65) Prior Publication Data
US 2018/0199976 A1 Jul. 19, 2018

(30) Foreign Application Priority Data

Jul. 10, 2015 (EP) ..................... 15176350

(51) Int. Cl.
*A61B 18/02* (2006.01)
*A61B 18/00* (2006.01)
(Continued)

(52) U.S. Cl.
CPC .......... *A61B 18/02* (2013.01); *A61B 18/0218* (2013.01); *A61B 2018/0022* (2013.01);
(Continued)

(58) Field of Classification Search
CPC ................ A61B 18/02; A61B 18/0218; A61B 2018/00023; A61B 2018/00095; A61B 2018/0022; A61B 2018/00351
See application file for complete search history.

(56) References Cited

U.S. PATENT DOCUMENTS

| 5,603,333 A | 2/1997 | Konings |
| 5,673,704 A | 10/1997 | Marchlinski et al. |

(Continued)

FOREIGN PATENT DOCUMENTS

| EP | 2294997 A1 | 3/2011 |
| WO | 2011151354 A2 | 12/2011 |

(Continued)

OTHER PUBLICATIONS

Examination Report issued in parallel Canadian patent Application No. 2,991,943, dated Sep. 17, 2018, 6 pages.

(Continued)

*Primary Examiner* — Michael F Peffley
*Assistant Examiner* — Bo Ouyang
(74) *Attorney, Agent, or Firm* — Lewis Roca Rothgerber Christie LLP

(57) ABSTRACT

A catheter device for ablating biological material is described. The catheter device comprises (a) a longitudinal structure; (b) an applicator for ablating the biological material, wherein the applicator is installed at the longitudinal structure; (c) a first electrode being attached to the longitudinal structure; (d) a second electrode being attached to the longitudinal structure; (e) an interface being connected directly or indirectly to the longitudinal structure; (f) a first lead electrically connecting the first electrode with the interface; and (g) a second lead electrically connecting the second electrode with the interface. The interface is configured for electrically connecting the first lead and the second (Continued)

lead with a measurement device for electrically stimulating the first electrode and the second electrode and for detecting an electric quantity being associated with an electric response of an biological material being located in between the two stimulated electrodes. Further, a catheter system with such a catheter device is described.

18 Claims, 16 Drawing Sheets

(51) Int. Cl.
  *A61B 18/12* (2006.01)
  *A61B 18/14* (2006.01)
(52) U.S. Cl.
  CPC ............ *A61B 2018/00023* (2013.01); *A61B 2018/0072* (2013.01); *A61B 2018/00095* (2013.01); *A61B 2018/00351* (2013.01); *A61B 2018/00577* (2013.01); *A61B 2018/00702* (2013.01); *A61B 2018/00732* (2013.01); *A61B 2018/00767* (2013.01); *A61B 2018/00797* (2013.01); *A61B 2018/00839* (2013.01); *A61B 2018/00875* (2013.01); *A61B 2018/00892* (2013.01); *A61B 2018/0212* (2013.01); *A61B 2018/0262* (2013.01); *A61B 2018/124* (2013.01); *A61B 2018/1407* (2013.01)

(56) References Cited

U.S. PATENT DOCUMENTS

| | | | |
|---|---|---|---|
| 5,782,760 A * | 7/1998 | Schaer | A61B 5/0422 600/381 |
| 6,423,057 B1 | 7/2002 | He et al. | |
| 6,471,694 B1 | 10/2002 | Kudaravalli et al. | |
| 6,635,053 B1 | 10/2003 | Lalonde et al. | |
| 7,070,594 B2 | 7/2006 | Sherman | |
| 7,842,031 B2 | 11/2010 | Abboud et al. | |
| 8,353,900 B2 | 1/2013 | Jung et al. | |
| 8,777,936 B2 | 7/2014 | Fischer et al. | |
| 2001/0016688 A1 | 8/2001 | Moore et al. | |
| 2005/0177146 A1 | 8/2005 | Sherman | |
| 2007/0255162 A1 | 11/2007 | Abboud et al. | |
| 2009/0182318 A1* | 7/2009 | Abboud | A61B 5/0538 606/21 |
| 2013/0338530 A1 | 12/2013 | Kassab | |
| 2016/0331262 A1* | 11/2016 | Kuck | A61B 5/0464 |

FOREIGN PATENT DOCUMENTS

| | | |
|---|---|---|
| WO | 2014138867 A1 | 9/2014 |
| WO | 2015049784 A1 | 4/2015 |

OTHER PUBLICATIONS

Chierchia, Gian-Battista et al., "Pulmonary vein isolation during cryoballoon ablation using the novel Achieve inner lumen mapping catheter: a feasibility study", Clinical Research, Ablation for Atrial Fibrillation, European Society of Cardiology, Eurospace (2012) 14, 962-967, Downloaded from http://europace.oxfordjournals.org/by guest on Sep. 16, 2014, 6 pages.
Deno, D. Curtis et al., "Measurement of Electrical Coupling Between Cardiac Ablation Catheters and Tissue", IEEE Transactions on Biomedical Engineering, vol. 61, No. 3, Mar. 2014, 10 pages.
Edd, Jon F. et al., "Imaging cryosurgery with EIT: tracking the ice front and post-thaw tissue viability", NIH Public Access, Author Manuscript; Physiol Meas. Aug. 2008; 29(8): 899-912, doi:10.1088/0967-3334/29/8/004, 18 pages.
Giumera, A et al., "Method and device for bio-impedance measurement with hard-tissue applications", Institute of Physics and Engineering in Medicine, Physiol. Meas. 29 (2008) S279-S290, doi:10.1088/0967-3334/29/6/S24.
Handler, Michael et al., "Computer simulation of cardiac cryoablation: Comparison with in vivo data", Medical Engineering & Physics 35 (2013) 1754-1761, www.elsevier.com/locate/medengphy, 9 pages.
Kaufman, Cary S. et al., "Office-based ultrasound-guided cryoablation of breast fibroadenomas", The American Journal of Surgery, 184 (2002) 394-400, 7 pages.
Kinouchi, Y. et al., "Fast in vivo measurements of local tissue impedances using needle electrodes", Medical & Biological Engineering & Computing, Sep. 1997, 35, 486-492, 2 pages.
Koruth, Jacob S., et al., "Occurrence of Steam Pops During Irrigated RF Ablation: Novel Insights from Microwave Radiometry", Journal of Cardiovascular Electrophysiology, vol. 24, No. 11, pp. 1271-1277, Nov. 2013, 7 pages.
Kreyszig, John Wiley & Sons Inc., Chap. 10, Sec. 10.10 Fourier Series, Integrals,and Transforms, pp. 569-579, 11 pages.
Radebaugh, Ray, "Heat Transfer Issues in Cryogenic Catheters", Cryogenic Technologies Group, S. Kakac et al. (eds), Microscale Heat Transfer, pp. 445-464, 2005, 20 pages.
Slepian, Marvin J. et al., "Multifunctional balloon catheters of the future", Interv. Cardiol. (2011) 3(4), 417-419, ISSN 1755-5302, 4 pages.
Tse, Hung-Fat et al.,"Effects of Temporal Application Parameters on Lesion Dimensions During Transvenous Catheter Cryoablation", Journal of Cardiovascular Electrophysiology, vol. 16, No. 2, Feb. 2005, pp. 201-204, 4 pages.
Examination Report issued in parallel Canadian Patent Appln. No. 2,991,943, dated May 26, 2020, 5 pages.

\* cited by examiner

ABLATION CATHETER DEVICE WITH ELECTRODES FOR DETECTING AN ELECTRIC RESPONSE OF BIOLOGICAL MATERIAL

CROSS-REFERENCE TO RELATED APPLICATIONS

This application is a National Phase Patent Application of International Patent Application Number PCT/EP2016/066107, filed on Jul. 7, 2016, which claims priority of European patent application no. EP 15176350.5 filed Jul. 10, 2015, the disclosures of which are hereby incorporated herein by reference.

TECHNICAL FIELD

Embodiments of the invention relate to the technical field of catheter devices which are configured to be used for ablating biological material. Further, embodiments of the invention relate to a catheter system with such a catheter device.

ART BACKGROUND

Therapeutic ablation is the intended, controlled destruction of tissue in the human body or in animals for treating for example cardiac arrhythmia, cancer or hypertension. Several methods are described in the art for guiding or monitoring a corresponding ablation process. For guiding the ablation process, for example, the contact of a catheter tip with the tissue can be assessed by measuring a contact force or an electrical impedance between the catheter tip and the tissue to be ablated (see U.S. Pat. No. 5,673,704). For monitoring the ablation process the temperature of the catheter tip or of the ablated tissue can be recorded (see Koruth et al.; "Occurrence of steam pops during irrigated RF ablation: novel insights from microwave radiometry"; J. Cardiovasc Electrophysiol 24, 2013).

For ablating tissue respectively biological material various sources of energy can be used such as for example radio frequency, focused ultrasound and/or laser radiation. Further, it is also known an approach to use a cryo-thermal destruction of biological material for ablating tissue of the human or animal body.

For radio frequency catheters U.S. Pat. No. 6,423,057 describes a change of capacitive tissue properties as an indicator for a lesion formation during a heating of tissue. For example laser balloon catheters offer the possibility to display the site of application by endoscopic devices. Cryo-thermal ablation can be assessed by imaging ice-ball formation using ultrasound (Kaufman et. al.; "Office-based ultrasound-guided cryoablation of breast fibroadenomas"; Am. J. Surg. 184, 2002). In preclinical experimental settings also electrical impedance tomography has been applied for imaging ice formation and lesion size (Edd et al. 2008; "Imaging cryosurgery with EIT: tracking the ice front and post-thaw tissue viability"; Physiol. Meas. 29, 2008). U.S. Pat. No. 7,070,594 discloses a method which uses a measurement current that becomes essentially zero when an ice-ball has been formed during a cryo-ablation procedure and, correspondingly, a measured "biological impedance" is significantly increased. In U.S. Pat. No. 7,842,031 impedance measurements are applied to increase the functional safety of cryo-ablation catheters by detecting refrigerant leaks by monitoring a change in a "biological impedance" value.

The basic function of cryo-thermal ablation catheters and principles of ice-formation in tissue are described for example in (Radebaugh; Heat transfer issues in cryogenic catheters; S. Kakac et al. (eds.); Microscale Heat Transfer; 2005) and (Handler et al.; Computer simulation for cardiac cryo-ablation: comparison with in vivo data; Medical Engineering & Physics 35, 2014).

Cryo-ablation consoles are devices delivering refrigerant to cryo-thermal catheters. They control cooling power and ensure functional safety of the cryo-ablation process. Typically, these devices contain computer systems providing control and user interface. Methods describing refrigerant supply and safety features are disclosed e.g. in U.S. Pat. No. 6,471,694 B2.

There may be a need for providing a catheter device and a catheter system having such a catheter device which allow for an easy an precise determination of an electric impedance of biological material which is supposed to be ablated or which is located in close proximity to a biological material to be ablated.

SUMMARY

This need may be met by the subject matter according to the independent claims. Advantageous embodiments of the present invention are described by the dependent claims.

According to a first aspect there is provided a catheter device for ablating biological material, in particular for ablating muscle tissue of the human or animal heart. The provided catheter device comprises (a) a longitudinal structure; (b) an applicator for ablating the biological material, wherein the applicator is installed at the longitudinal structure; (c) a first electrode being attached to the longitudinal structure; (d) a second electrode being attached to the longitudinal structure; (e) an interface being connected directly or indirectly to the longitudinal structure; (f) a first lead electrically connecting the first electrode with the interface; (g) a second lead electrically connecting the second electrode with the interface. The interface is configured for electrically connecting the first lead and the second lead with a measurement device for electrically stimulating the first electrode and the second electrode and for detecting an electric quantity being associated with an electric response of an biological material being located in between the two stimulated electrodes.

The described catheter device is based on the idea that by providing an electrode configuration in connection with an interface allowing to electrically connect the catheter device with an appropriate measurement device detailed and precise measurements of impedances of portions of biologic material can be carried out.

The first electrode may be a so called tip electrode (in case it is formed at the tip of the longitudinal structure. The first electrode serves primarily for a measurement procedure resulting in the electric quantity. However, the first electrode may also be involved in an ablating procedure of the biological material. In case of a cryogenic ablation the first electrode may adopt a low temperature.

Further, the described applicator serves primarily for ablating the biological material. In case of a cryogenic ablation the applicator is the most important element to be cooled and to be brought into contact with the biological material being supposed to be ablated. However, when being electrically connected in a proper way the applicator can serve as an electrode which can be used for measuring respectively for detecting the electric quantity.

The applicator and the first electrode may be realized by means of a common electrically and/or thermally conductive structure. Although this may result in a poorer spatial resolution for detecting the electric quantity a manufacturing of the described catheter device may be simplified and the resulting catheter device may be sufficient in particular for comparatively simple applications. In this respect it is mentioned that the applicator can also be connected with appropriate electric leads extending between the interface and the respective portion of the applicator. By this way the effective size of the first electrode can be varied.

The described applicator can be realized by means of a tube structure. The first electrode can be a cover structure covering or closing the tube structure. In case of a common electrically and/or thermally conductive structure the cover structure is electrically connected with the tube structure. In case the applicator and the first electrode are separated from each other there is at least an electrical insulation between the cover structure and the tube structure.

The electric quantity may be a voltage (drop between the two electrodes) and/or a current flowing through the biological material being located between the two electrodes.

The detected electric quantity may be an electric impedance being indicative for the temperature of the described biological material. The impedance may be defined by a real part corresponding to an active current or in-phase current and by an imaginary part corresponding to a reactive current.

The electric contact between the first electrode and the tissue may be established by means of a direct contact and/or by means of a capacitive coupling.

According to an embodiment the catheter device comprises at least one further second electrode, wherein the second electrode and the further second electrode are electrically connected in parallel. This may mean that there is at least one further second lead which connects the at least one further second electrode with the interface. Such a configuration of the catheter device may provide the advantage that a small (unwanted) impedance may be achieved in a current return path of the wiring being needed for detecting an electric quantity. A small impedance of the current return path may allow to measure the "biological impedance" with a high accuracy.

It is mentioned that a parallel electrical connection between the second electrode and the further second electrode can also be realized by means of only the second lead (i.e. there is no further second lead), wherein the only one second lead connects to both electrodes. This may provide the advantage that the wiring effort can be reduced significantly.

According to a further embodiment the catheter device comprises an insulating structure which provides for an electrical insulation between the biological material and the first electrode.

The described insulating structure may result in an increased operational safeness of the entire catheter device. This increased operational safeness may be in particular relevant if, e.g. because of a failure of the measurement device, the first electrode is at a voltage level which, under a direct contact with the biological material, could be dangerous for the human or animal body being under treatment.

According to an embodiment the applicator is a cryogenic applicator and the catheter device further comprises (a) a first fluid line extending between the interface and the cryogenic applicator and being configured for feeding a cooling fluid to the cryogenic applicator; and (b) a second fluid line extending between the cryogenic applicator and the interface and being configured for discharging the cooling fluid from the cryogenic applicator.

The described interface may not only be a pure electric interface but also an interface allowing for a media transfer, which media is used or at least contributes to the ablation process.

The cooling fluid may be any material which is capable of reducing the temperature of the applicator. In particular, the cooling fluid may be nitrous oxide N2O. During operation of the described catheter device the cooling fluid may be transported to the cryogenic applicator via the in first fluid line in essentially liquid or supercritical form. At the applicator the cooling fluid may be vaporized in order to effectively cool the cryogenic applicator. The vaporized cooling fluid will then be transported back to the interface via the second fluid line predominantly in gaseous form.

The above described measurement device may be realized or build up within a central console device which may also include an ablation unit being configured for handling the cooling fluid. Preferably, the cooling fluid is handled within a closed or open loop.

According to a further embodiment the catheter device comprises (a) a first boiling chamber being in thermal contact with the cryogenic applicator and being designed to operate at a first flow rate of the cooling fluid and (b) a second boiling chamber being in thermal contact with the cryogenic applicator and being designed to operate at a second flow rate of the cooling fluid, wherein the first flow rate is higher than the second flow rate.

By appropriately adjusting the two flow rates it might be achieved that the cooling fluid boils at a pressure being larger that the pressure being assigned to the triple point of the cooling fluid. This may provide the advantage that the cooling fluid cannot be transformed into a solid phase and, thus, it can flow through the catheter device.

In a preferred spatial configuration the two boiling chambers are part of a rotational symmetric geometry of at least a proximal portion of the described catheter device. Thereby, one boiling chamber, preferably the first boiling chamber, is an inner boiling chamber and the other boiling chamber, preferably the second boiling chamber, is an outer boiling chamber.

According to a further embodiment the longitudinal structure comprises (a) a shaft; (b) a positioning device being movable along an axis of the shaft; and (c) a distal member being mounted at a distal end of the positioning device.

Descriptive speaking, by moving the positioning device with respect to the shaft the distal member, which is attached to the positioning device, will be longitudinally shifted with respect to the shaft. The above described applicator may extend between the distal and of the shaft and a proximal and of the distal member. This has the effect that by moving the positioning device the spatial configuration of the applicator will be changed.

For inserting the catheter device through a blood vessel respectively through a vein or an artery the applicator will be stretched into a longitudinal shape being oriented more or less coaxially with the axis of the shaft. At the location at which the cryogenic ablation is supposed to be accomplished, the positioning device is moved relative to the shaft in such a manner that the distal member approaches that shaft. As a consequence, the longitudinal shape of the applicator will be transformed into an appropriate three dimensional form allowing for an ablation of biological material.

It is mentioned that in connection with similar catheter designs the positioning device is often also denominated a positioning catheter. Further, the distal member is often called a tip portion of the entire catheter device.

In order to facilitate a handling of the entire catheter device the catheter device may be provided with an appropriate handle being formed at the proximal end of the shaft.

According to a further embodiment the applicator extends between a distal end of the shaft and a proximal end of the distal member and, in an operational state allowing for ablating biological material, the applicator adopts either a loop shape or a balloon shape. In a preferred embodiment the loop shape may be a helical shape.

At this point it is mentioned that in accordance with the basic principles of ablation catheter devices the loop shape respectively the balloon shape is not adopted during an insertion of the catheter device into the human or animal body through a blood vessel respectively through an artery or vein.

According to a further embodiment the catheter device further comprises (a) a diagnostic device being insertable and/or shiftable within the longitudinal structure comprising diagnostic electrodes for recording electrical signals being associated with a physiological function of a human or animal body being treated with the catheter device; and (b) a wiring arrangement electrically connecting the diagnostic electrodes with the interface.

The diagnostic device may also comprise a spatial structure which can adopt different spatial configurations. The first spatial configuration may be required when the diagnostic device is moved within the longitudinal structure in order to insert that the diagnostic device into the body being supposed to be treated. The second spatial configuration may be needed in order to perform the electric measurements being associated with the desired diagnostic function.

The diagnostic function may be in particular an electrocardiogram (ECG) and/or biopotentials created by other muscle cells or neurons. However, it may also be possible that other electric actions of functional body parts can be investigated.

In the second configuration the described diagnostic device may comprise any appropriate shape (depending on the specific application). In particular, the appropriate shape may have a bending portion and a distal member wherein both portions are located at least approximately within a common plane or layer. Alternatively the diagnostic device may comprise a shape which comprises a bending portion and spirally formed distal member.

According to a further embodiment the diagnostic device comprises a shaft diameter which is smaller than 1.5 mm and in particular smaller than 1.1 mm.

The shaft diameter may be in particular the spatial dimension of the diagnostic device measured perpendicular to its longitudinal extension. In this respect it is pointed out that it is not necessary that the longitudinal extension follows a straight line. It may also be possible that the longitudinal extension follows a curved line and in particular a spiral line.

A small or narrow geometry of the diagnostic device may allow for recording of ECGs and/or pacing of tissue with one pair of electrodes. By rotating the diagnostic device around its longitudinal axis any location in azimuthal direction can be investigated by ECG recordings and/or pacing with only one pair of electrodes. Thus, the diagnostic device can be built with a small diameter as only one pair of electrodes is needed for ECG measurement and pacing.

According to a further embodiment at least some of the diagnostic electrodes provided on or at the diagnostic device are arranged in a pairwise manner.

In this respect "arranged in a pairwise manner" may mean that along the linear or preferably non-linear extension of the diagnostic device respectively (at least) two electrodes are provided with a close distance to each other whereas the distance to other diagnostic electrodes is much larger.

The described "paired arrangement" of the diagnostic electrodes may provide the advantage that a high spatial resolution can be achieved when measuring ECGs. Further, a local pacing of tissue is possible.

According to a further embodiment a distance D between a loop plane of the catheter device and a loop plane of the diagnostic device is smaller than 40 mm, in particular smaller than 30 mm.

In this respect the term "loop plane" may refer to a plane within three dimensional space within which a loop portion of the respective device, i.e. the catheter device and the diagnostic device, is located. Having a small distance between these two loop planes allows the diagnostic device to perform measurements in close proximity to the treatment region of the ablation catheter. By this way the diagnostic electrodes may be brought into contact with myocardium in the atria for measuring ECGs.

According to a further embodiment the first electrode comprises (a) a first portion for contacting the tissue; and (b) a second portion being contactable with cryogenic fluid, wherein the second portion comprises a surface contour increasing the thermal interaction area between the cryogenic fluid and the first electrode. By increasing the thermal interaction area respectively the thermal interaction region the thermal inertia of the first electrode and in particular of its first (tip) portion will be decrease. As a consequence, a temperature dependent electrical response of the biological material can be determined pretty fast and in a reliable manner.

According to a further embodiment the catheter device further comprises (a) at least one further first electrode; (b) a lead arrangement electrically connecting the at least one further first electrode with the interface. This may provide the advantage that with the described catheter device not only one impedance measurement is possible but at least one further impedance measurement can be carried out simultaneously. Depending on the spatial location of the first electrode and the at least one further first electrode the electric response of different body portions can be investigated.

Preferably, the described catheter device comprises not only two but a plurality of first electrodes. This may allow for simultaneously measuring a detailed electric response of a plurality of different portions of biological material.

According to a further aspect there is provided a catheter system comprising (a) a catheter device as described above; and (b) the measurement device, wherein the measurement device comprises (b1) a stimulating unit for electrically stimulating the first electrode and the second electrode; (b2) a detecting unit for detecting the electric quantity received from the two electrodes; and (b3) a computing unit for determining, based on the detected electric quantity, an electric impedance of the biological material being located in between the two stimulated electrodes.

The described catheter system is based on the idea that with appropriate electronic circuits being connectable respectively being connected to the electrodes of the catheter device (via the interface) an impedance measurement and, in particular in case the applicator is a cryogenic applicator a temperature dependent impedance measurement, can be carried out in an effective and reliable manner.

The described electric quantity being detected by the detecting unit may be a either a voltage (between the two electrodes) or a current flowing via the two electrodes and the biological material being located therebetween.

The computing unit may not only be used for an analysis of the detected electric quantity but also for controlling the stimulating unit. In this way appropriate measurement procedures can be controlled. Such measurement procedures may be predefined measurement procedures, wherein depending on the specific application an appropriate predefined measurement procedure can be selected.

For practical reasons in particular when operating respectively handling the described catheter system the stimulating unit, the detecting unit and, if applicable also the computing unit may be arranged within a console wherein the user, in particular a physician, can control all electric power matters when ablating biological material. In case the applicator is a cryogenic applicator such a console may also include a cooling fluid handling unit which may be used for delivering the cryogenic fluid towards the distal end of the catheter device.

According to a further embodiment the stimulating unit is configured for stimulating the first electrode and the second electrode with an adjustable electric amplitude. This may provide the advantage that depending on the specific application an appropriate strength of electrical stimulation can be used. Thereby, the appropriate strength of electrical stimulation may depend on the type and/or on the temperature of the biological material the impedance of which is supposed to be measured.

The described electric stimulation may comprise charging respectively loading the electrodes with a certain voltage. Alternatively or in combination the electric current flowing between the electrodes and the biological material being located therebetween can be set by means of the stimulating unit.

According to a further embodiment the stimulating unit comprises (a) a reference signal generator; and (b) a voltage and/or current source operable in response to the reference signal generator. Thereby, the voltage and/or current source is connected to the interface of the catheter device.

By controlling the operation of the described reference signal generator, in particular by means of the above mentioned computing unit, the strength of the electric stimulation can be controlled in an easy and effective manner.

According to a further embodiment the stimulating unit comprises a switching unit for changing in a discrete manner the strength of stimulating the first electrode and the second electrode. This may provide the advantage that an appropriate strength of the stimulation can be easily selected. Further, the respective strength can be characterized by a very precise level of the respective electric stimulation.

The switching unit may be located respectively connected between (i) the above described reference signal generator and (ii) the interface of the catheter device. The operation of the switching unit may be controlled by the above described computing unit.

According to a further embodiment the stimulation unit is configured to change, preferably driven by the switching unit, a stimulating quantity for the first electrode and the second electrode from a first level to a second level, wherein the second level is smaller than the first level by at least a factor of 10, preferably by at least a factor of 100.

This may provide the advantage that a quick change between different measurement ranges for measuring electric impedances can be accomplished. Specifically, when the applicator is moved forwardly an impedance measurement may be used for detecting a wall contact between (a) the first electrode and/or the second electrode on the one hand and (b) tissue on the other hand. During this "moving forward" the impedances are typically comparatively low. Therefore, the first (high) level of stimulation should be used. By contrast thereto, when during a cryo ablation a formation of frozen tissue occurs, the measured impedance increases significantly. Therefore, the second (low) level of stimulation should be used for obtaining a good signal quality.

The stimulating quantity may be any AC electric quantity, such as voltage or current. Preferably, for performing high quality impedance measurements the stimulating quantity is an AC current having preferably a frequency in the range between 5 kHz and 200 kHz.

It is mentioned that the described change from the first level to the second level (and vice versa from the second level to the first level) can be accomplished in a smooth or continuous manner. However, preferably there is a discrete change between the two levels such that switching the measurement range can be realized in a short duration of time.

Also in this context it is pointed out that it is of course also possible to operate with more than two stimulation levels. Thereby, a higher number of measurement ranges and, as a consequence, more precise measurements can be carried out.

According to a further embodiment the first level is an AC current below 0.15 mA or more specifically below 0.1 mA. Thereby, the described current level preferably refers to a peak level of the AC current. At the second level the current is below 0.01 mA. By using such low stimulation currents the output voltage of the stimulation unit can be kept below 0.05 V. By reducing current and voltage to low levels unintended stimulation of tissue can be avoided even when operating the system at a low operation frequency of the stimulation unit. Furthermore, interference with other devices in clinical use can be reduced.

It is mentioned that an AC current with the first level may be used for detecting a wall contact between (a) the first electrode and/or the second electrode on the one hand and (b) tissue on the other hand. The second level may be applied for recognizing a formation of ice within the biological material being located in between the two stimulated electrodes.

According to a further embodiment the stimulating unit comprises a multiplexing unit being connected with the interface. The multiplexing unit and the interface are configured for stimulating the first electrode and/or the at least one further first electrode. Further, wherein one channel of the multiplexing unit is assigned to one of the electrodes.

The described embodiment comprising the multiplexer unit may be in particular of advantage in case the catheter device comprises a plurality of electrodes (first electrode and further first electrodes) which, by means of the multiplexer unit, can be controlled respectively operated in parallel. This may lead to a significant speed up of a measurement procedure wherein a plurality of biological material portions are investigated in particular with respect to their electric responses when being electrically stimulated by the plurality of electrodes.

According to a further embodiment the measurement device comprises means for splitting the detected electric quantity into a real part and into an imaginary part, wherein the computing unit is configured for comparing the real part with the imaginary part and for determining, based on the result of comparing, the electric impedance of the biological material. This may provide the advantage that a formation of ice can be recognized in a particular reliable manner.

Thereby, benefit can be taken from the following insight: When biological material freezes there is a significant change in both the real part of the impedance and the imaginary part of the impedance, whereby however the course of the impedance change of the real part is different that the course of the impedance change of the imaginary part. This has the effect that a phase angle of the detected (complex) electric quantity is a very sensitive measure for the formation of ice. Thereby, the phase angle may be given by tan (imaginary part/real part).

It is mentioned that depending on the specific application appropriate thresholds may be defined which are considered to indicate a formation of ice. As an example, a phase angle of 45° (i.e. the magnitudes of the real part and the imaginary part are the same) may be an appropriate threshold. Of course, also thresholds may be defined which also take into account the magnitude of the electric quantity, which magnitude may be the resistivity of the biological material. Thereby, the magnitude may be given by the square root of (real part)^2+(imaginary part)^2.

According to a further embodiment the stimulating unit is configured for stimulating the first electrode and the second electrode at an operating frequency between 6 kHz and 24 kHz and more particular between 10 kHz and 18 kHz. Within these operating frequency ranges the temperature profile of both the magnitude and the phase of the detected electric quantity respectively the determined impedance undergoes significant changes. This may allow both for a sensitive and a reliable cognition of a formation of ice.

According to a further embodiment the stimulating unit comprises a first protection circuit being assigned to the second electrode and being configured for limiting a current flow to and/or from the second electrode. Alternatively or in combination the detecting unit comprises a second protection circuit being assigned to the first electrode and to the second electrode and being configured for keeping a voltage level between the first electrode and the second electrode within a predefined range.

By limiting, by means of the first protection circuit, the current flow being associated with the second electrode unwanted electrical injuries of a human or animal being subjected to an ablating procedure can be prevented.

In a simple realization the first protection circuit may comprise a resistor and/or a capacitor. Thereby, the resistor may limit in particular a DC current and the capacitor may limit in particular an AC current. Preferably, the first protection circuit may comprise or may consist of a serial connection between a resistor and a capacitor.

By limiting, with the help of the second protection circuit, voltage levels being possibly dangerous for a human or animal being subjected to an ablating procedure can be prevented.

The second protection unit may be a diode based electric circuit, which is configured in order to keep the voltage level between a positive supply voltage and a negative supply voltage for the entire measurement device. A person skilled in the art having some knowledge about the effect of diodes within electric circuits will be able to realize the second protection unit with many different appropriate circuits. In this respect it is mentioned that a width of an acceptable voltage level between the positive supply voltage and the negative supply voltage may be diminished by known voltage drops of semiconductor diodes.

According to a further embodiment the detecting unit comprises a third protection circuit being connected between the computing unit and other electronic components of the detecting unit. Alternatively or in combination the measurement device comprises a fourth protection circuit being assigned to a power input of the measurement device and preventing over-voltages and/or over-currents being generated by an external power source from reaching the measurement device.

The described third protection circuit may allow for separating the detecting unit from the computing unit with respect to voltage levels which could be harmful. Specifically, the third protection circuit may prevent that voltage peaks being produced by or occurring within one of these units result in a damage of the other one of these units. This increases the operational safety of the entire catheter system.

The mentioned other electronic components may include for instance an isolation instrumental amplifier (a floating electronic component having no ground contact terminal) and/or an insolation operational amplifier (having on terminal connected to ground).

The third protection circuit may be configured in order to realize a galvanic separation between the computing unit and the electronic components of the detecting unit. To this end the first protection circuit may comprise at least one optoelectronic coupler including a light emitting diode (LED) and a photodiode being optically and communicatively coupled with the LED.

In a preferred embodiment the first protection circuit includes two optoelectronic couplers. Thereby, one optoelectronic coupler is assigned to a signal path carrying signals propagating from the detecting unit towards the computing unit. The other optoelectronic coupler is assigned to another signal path carrying signals propagating from the computing unit towards the detecting unit.

The described fourth protection circuit may allow for protecting the measurement device and also the entire catheter system from being harmed by external over-voltages and/or over-currents which might occur in external power sources for instance in response to a lightening stroke.

The fourth protection circuit may also provide for a galvanic separation at the power input of the measurement device. The galvanic separation may be realized for instance by means of a switching arrangement comprising at least two switches and a capacitance located in between the two switches. Thereby, the two switches are controlled in such a manner that there is no operational state in which both switches are closed. Another possibility for realizing a galvanic separation is the use of a so-called DC-DC coupler. Such a DC-DC coupler may comprise a serial connection between (a) a DC-AC converter, (b) a transformer, and (c) a AC-DC converter.

According to a further embodiment the stimulating unit comprises a signal generator which is configured to generate pulses of finite duration containing frequency components between a low frequency value and a high frequency value. Further, the signal generator is configured for electrically stimulating the first electrode and the second electrode with the generated pulses. This may allow for a quick assessment of impedances in a given and appropriate frequency band.

According to a further embodiment the stimulating unit further comprises a multiplexing unit receiving the generated pulses and being configured for sequentially stimulating a plurality of first electrodes. Depending on the spatial configuration of the electrodes and in particular of the first electrode(s) these impedances can be measured at multiple locations within a region containing the biological material to be ablated.

According to a further aspect there is provided a method for ablating biological material, in particular for ablating muscle tissue of the human or animal heart. The provided method comprises (a) ablating the biological material with an applicator of a catheter device as described above; (b) electrically stimulating the first electrode and the second electrode; and (c) detecting an electric quantity being associated with an electric response of an biological material being located in between the two stimulated electrodes.

Also the described method is based on the idea that by providing a catheter device with an electrode configuration in connection with an interface allowing to electrically connect the catheter device with an appropriate measurement device detailed and precise measurements of impedances of portions of biologic material can be carried out.

According to a further embodiment ablating the biological material comprises (a) cooling down the applicator by means of a cooling fluid; and (b) extracting heat from the biological material such that the biological material is irreversibly harmed. This may allow for an effective ablating procedure.

In this context it has been found out that the electric impedance of biological material strongly depends on the temperature of the biological material. This holds in particular if the temperature is so small, e.g. smaller than 0° C., that the biologic material is in a frozen state. This means that the electric impedance can be used as a highly significant information about the temperature of the biological material. As a consequence, this information can be used in order to optimize the procedure of ablating the biological material.

According to a further embodiment the method further comprises performing a cooling cycle by repeatedly changing the flow rate of a cooling fluid being in thermal connection with the applicator in response to the detected electric quantity.

Since the above described impedance measurement allows for a determination of the temperature of the biological material being located between the two electrodes this temperature information can be used for estimating the spatial region wherein the biological material is in the frozen state. By means of an appropriate regulation respectively by means of an appropriate closed loop control of the flow rate it can be ensured that the cooling cycle is performed in such a manner that there is always at least a small portion of biological material in the frozen state. Since the tip of the catheter device will be frozen to this biological material the position of the applicator within the human or animal body will remain fixed. When maintaining the corresponding fixed position cooling cycles can be carried out where at least some biological material is repeatedly freezing and unfreezing, which in a known manner results in an effective ablation process.

According to a further embodiment the cooling cycle comprises operating the applicator repeatedly with a first flow rate of the cooling fluid and with a second flow rate of the cooling fluid, wherein the first flow rate is higher than the second flow rate and wherein the second flow rate is regulated in response the detected electric quantity.

The detected electric quantity may be in particular an impedance value which is meaningful for regulating the second flow rate in such a manner that the applicator remains frozen to the tissue under treatment.

It is mentioned that the described flow regulation may not only depend on the results of an impedance measurement but also in combination with an appropriate temperature measurement.

It is further mentioned that the term "tissue under treatment" might refer not only to the tissue which is supposed to be ablated but also to the surrounding tissue which experiences a significant cooling.

According to a further embodiment the detected electric quantity is monitored during a thawing of tissue occurring after a termination of freezing. Further, a warning is generated when the detected electric is above a threshold indicating that the applicator is frozen to the tissue. This may increase in a beneficial manner the operational safeness of the described catheter device because an unwanted spatial manipulation of the catheter device will only be prevented in a reliable manner while the catheter device is frozen to the tissue under treatment.

According to a further embodiment the detected electric quantity is provided by means of a logarithmic measure and/or logarithmic representation of the magnitude of the electric quantity at the output of a voltage divider structure. This may provide the advantage that the electric quantity and in particular the impedance value will be given with a high accuracy. Further, an assessment of the detected electric quantity respectively the impedance value can be used by a user, in particular by a physician, for intuitively interpreting a chance of the electric quantity respectively the impedance value as to be a formation of ice within the biological material being under treatment.

According to a further embodiment both the first electrodes and the second electrodes all being attached to the longitudinal structure are located within the inside of the human or animal heat. This may provide the advantage that for carrying out the described method electrodes on respectively at the body surface are not needed. This allows for a small cabling effort.

It has to be noted that embodiments have been described with reference to different subject matters. In particular, some embodiments have been described with reference to apparatus type claims whereas other embodiments have been described with reference to method type claims. However, a person skilled in the art will gather from the above and the following description that, unless other notified, in addition to any combination of features belonging to one type of subject matter also any combination between features relating to different subject matters, in particular between features of the apparatus type claims and features of the method type claims is considered as to be disclosed with this document.

The aspects defined above and further aspects are apparent from the examples of embodiment to be described hereinafter and are explained with reference to the examples of embodiment. Embodiments of the invention will be described in more detail hereinafter with reference to examples of embodiment but to which the invention is not limited.

DETAILED DESCRIPTION

Figure 1:
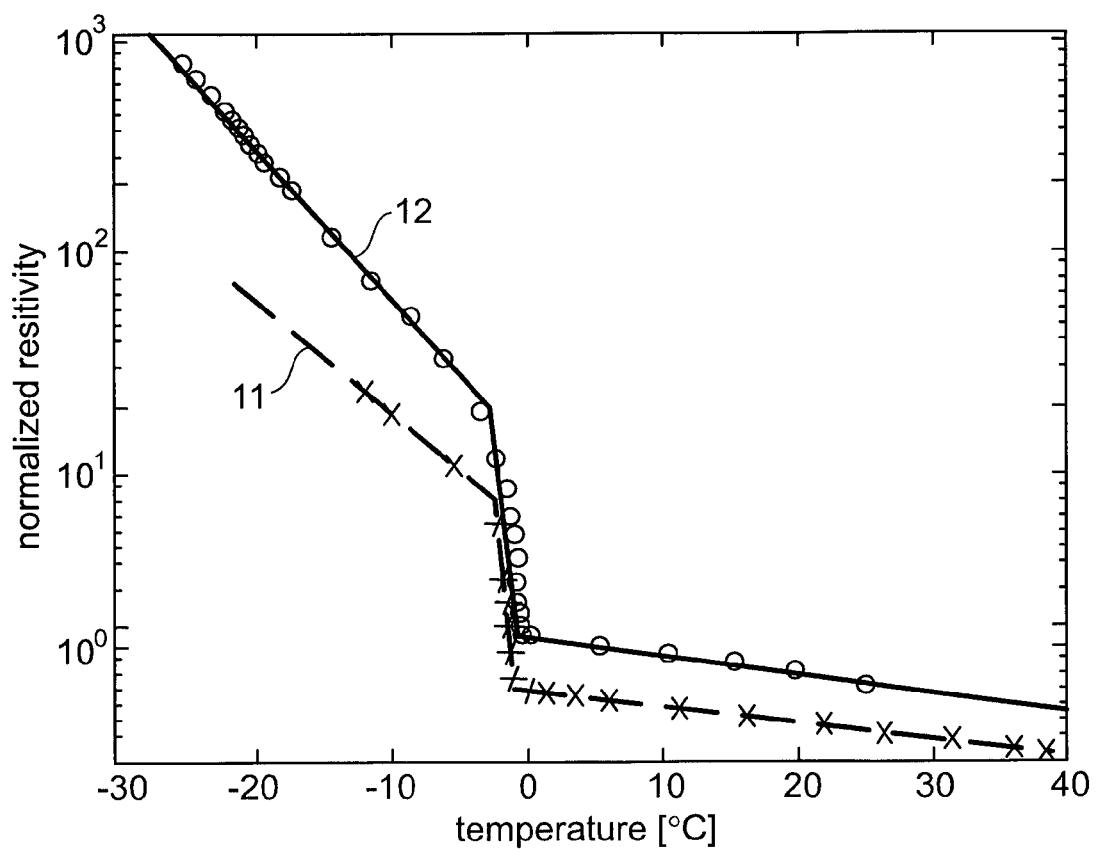
FIG. 1 shows the electrical conductivity of a physiological NaCl-solution and muscle tissue as a function of temperature.

The illustration in the drawing is schematic. It is noted that in different figures, similar or identical elements or features are provided with the same reference signs. In order to avoid unnecessary repetitions elements or features which have already been elucidated with respect to a previously described embodiment are not elucidated again at a later position of the description.

Further, spatially relative terms, such as "front" and "back", "above" and "below", "left" and "right", et cetera are used to describe an element's relationship to another element(s) as illustrated in the figures. Thus, the spatially relative terms may apply to orientations in use which differ from the orientation depicted in the figures. Obviously all such spatially relative terms refer to the orientation shown in the figures only for ease of description and are not necessarily limiting as an apparatus according to an embodiment of the invention can assume orientations different than those illustrated in the figures when in use.

During cryo-thermal or cryo-ablation a formation of ice forms or develops in tissue under treatment. The resulting physical transformation of body liquids to solid state is also associated with a change of electric properties, in particular conductivity and capacity. This change could be used for monitoring an ice formation and, thus, the progress of the ablation progress.

FIG. 1 shows the electrical conductivity of a physiological NaCl-solution and muscle tissue as a function of temperature. The temperature dependence of the NaCl-solution is given by curve 11, the temperature dependence of the muscle tissue is given by the curve 12. It has to be noted that a logarithmic scale is applied at the ordinate of the plot and conductivities are normalized by the conductivity of physiological NaCl-solution at zero degrees centigrade.

The curves 11 and 13 have been obtained experimentally. The respective measurements obtained for the physiological NaCl-solution are indicated by asterisks. The data is approximated by fitting piecewise linear segments indicated by hatched lines into the plot. Without being bound to a specific theory the following observations can be made: In the liquid phase (between body temperature and freezing point) a moderate increase of resistivity with progressing cooling (resulting in a decreasing of the temperature) can be observed. A few tenth of degrees centigrade below zero a freezing starts and the resistivity increases rapidly as the cooling process progresses. At approximately −2° C. most of the water content of the NaCl-solution is frozen and now a slower increase of resistivity with progressing cooling is observed. In the depicted plot the curve 11 is extrapolated down to −21° C., which is the eutectic temperature of a sodium chloride water solution.

A similar behavior is observed for cooling the muscle tissue. Here, the respective measurements are indicated by circles. A piecewise linear interpolation is made and indicated by the solid lines 12. As tissue contains a complex mixture of various ions, data show a continuous increase of resistivity with progressing cooling also below −21° C.

For the depicted examples the magnitude of a complex resistivity is shown. Here the change of resistivity is mainly influenced by an increase of ohmic resistivity. At high frequencies also capacitive effects might also contribute to the observed resistivity.

Thus, by freezing muscle tissue or another type of tissue the local resistivity might increase by several orders of magnitude. Proper technical means are requested for accurately and locally measuring this change of tissue properties over a wide range.

During a cryo-ablation process it is obvious that with the tissue under treatment the temperature is not spatially uniform. Pronounced temperature gradients might be observed.

Figure 2:
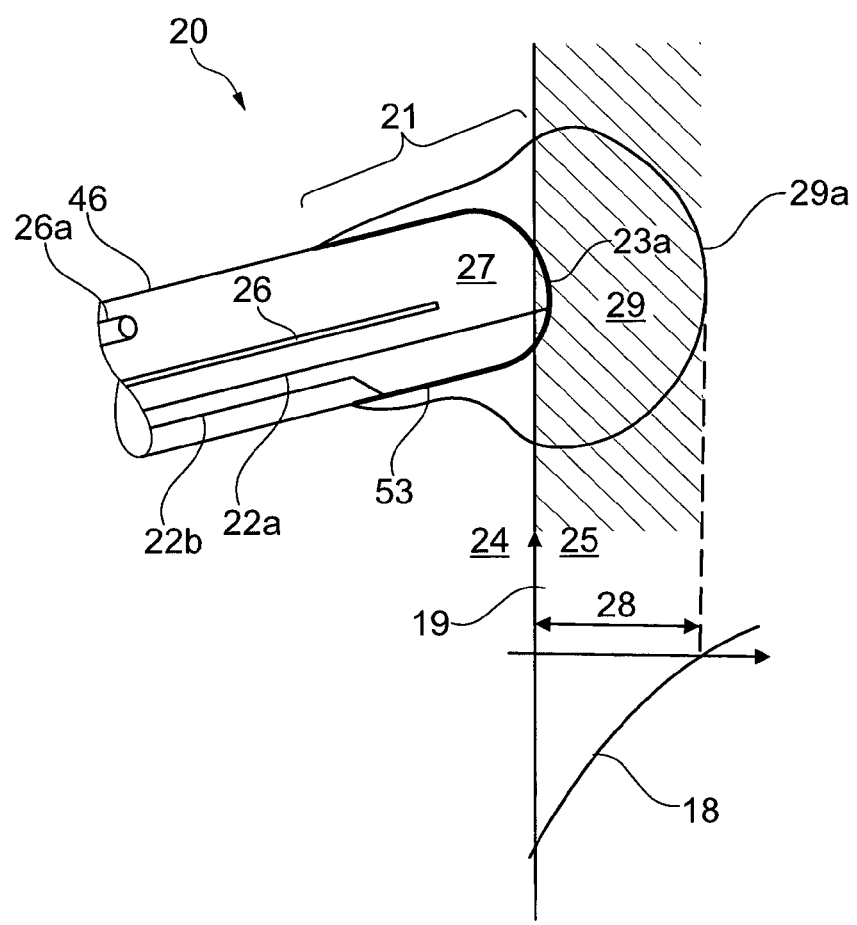
FIG. 2 shows a distal member of a cryo-ablation catheter in accordance with a first embodiment of the invention.

FIG. 2 depicts a cryo-ablation catheter 20 in accordance with an exemplary embodiment of the invention. The cryo-ablation catheter 20 comprises a distal cryo portion 21 being defined by a so called cryo-applicator 53.

An expected temperature profile, which occurs during a cryo-ablation procedure within the tissue under treatment 25, is denominated with reference numeral 18. Further, the potential shape of a frozen tissue region 29 is indicated. A tip portion 23a of the cryo-ablation catheter 20 is the main part being in contact with the tissue 25. The remaining portion of the cryo-applicator 53 is mainly surrounded by a blood pool 24, which can be e.g. a blood flow inside a cardiac cavity or vessel.

At least the surface structures of the tip portion 23a and the cryo-applicator 53 are made from a material with is a thermal and electric conductor (for example metal, carbon, electrically conductive plastics). These surface structures are used for achieving a plurality of functions. Firstly, they define a heat transfer interface between a boiling chamber 27 of the cryo-ablation catheter 20 and the tissue 25. Secondly, these surface structures are used as electrodes for recording impedances. Thirdly, according to the embodiment described here they are used as recording electrodes for sensing electrograms containing information about the physiological or pathophysiological function of the tissue 25.

In other embodiments these surface structures might be used for adding additional function as for example localization of the cryo portion respectively the catheter tip 21 by a navigation system.

A cryo-ablation procedure is started by supplying a cooling liquid respectively a refrigerant along a supply line 26 to the boiling chamber 27. A schematically depicted return line 27 is used for guiding back the (at least partially) vaporized refrigerant.

With performing a cooling, adjacent to the contact of the cryo portion 21 with the tissue 25 an ice layer forms. Inside the tissue 25 the shape of the frozen tissue region 29 might be approximated by a half sphere with a certain thickness 28. Low temperature and a high resistivity (compared to body temperature) might be observed close to the catheter tip 21. This can be seen from the temperature profile 18 where temperature is plotted on the ordinate of the depicted diagram. In a border zone 29a of the frozen region 29 moderate subzero temperatures and some increase of resistivity might be observed. In the portion of the catheter tip 21, which portion is surrounded by the blood flow 24, the size of the ice-layer might be reduced due to the thermal load imposed by the blood flow 24. As freezing progresses the temperature of the cryo-applicator 53 decreases and the thickness of the ice layer increases. This affects the resistivity of the tissue 25 surrounding the cryo-applicator 53. Thus, the electrical impedance between the properly located first electrode 23a and the body under treatment comprising the tissue 25 expected to increase as the volume of the frozen tissue region 29 increases. An electrode 46, hereinafter called second electrode 46, is foreseen to complete the current return path for respective impedance measurement.

It is to be noted that the surface structures of the first electrode 23a and the (rest of the) cryo-applicator 53 both contribute to a heat transfer from the cryo portion 21 to the body under treatment, here the blood pool 24 and tissue 25. The entire surface contributing to the heat transfer from the boiling chamber 27 to the body is the cryo-applicator 53. For the shown example most of this surface is formed by the structure 53. However, the respective heat transfer surface is split into two parts, i.e. the first electrode 23a and the cryo-applicator 53, which are electrically insulated from each other. Due to a small size of the first electrode 23a an accurate measurement of the local ice formation will be enabled, as will be described below with reference to FIG. 3.

Thus, the main function of the tip portion respectively the first electrode 23a is that of an impedance recording electrode allowing for a high spatial resolution.

According to the exemplary embodiment described here the first electrode 23a is connected with a non-depicted interface of the catheter device 20 via a lead 22a. In the following this lead is denominated a first lead 22a. Further, since the cryo-applicator 53 also serves as an electrode, there is a further lead 22b electrically connecting the cryo-applicator 53 with this interface.

Figure 3:
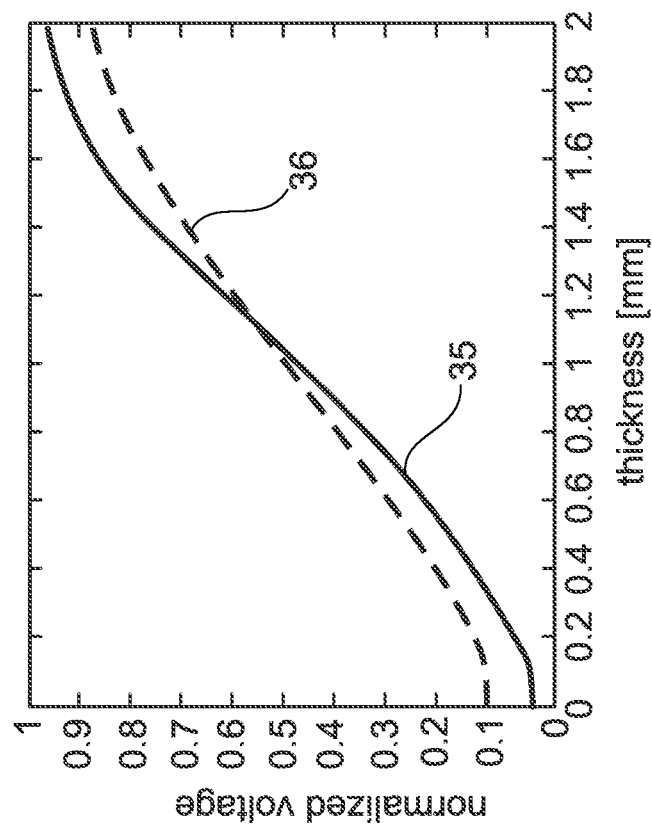
FIG. 3 shows impedance values as a function of material thickness in two different scales.
Figure 3:
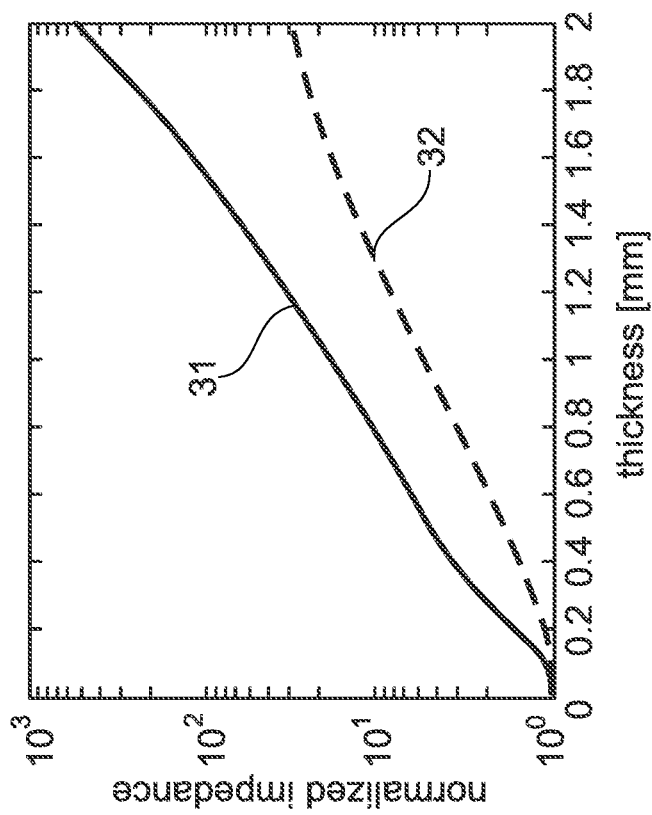

FIG. 3 shows impedance values as a function of material thickness in two different plots using different scales for its ordinate. In one plot depicted on the left side the normalized impedance is depicted in a logarithmic scale.

The electrode 23a shown in FIG. 2 is arranged such that it is mainly in contact with the tissue 25. Combining the temperature dependent resistivity data 12 depicted in FIG. 1 with the temperature profile 18 depicted FIG. 2 the tip-to-body impedance can be computed by means of computer modeling for any size or radius of the frozen tissue region 29. Trace 31 in FIG. 3 shows the tip-to-body impedance of the electrode 23a as a function of the thickness of the ice-layer. The shown impedance data is normalized by the tip-to-body impedance before freezing (i.e. the entire volume is at body temperature).

It has to be noted that with the logarithmic scale a continuous increase can be observed for the trace 31 which might be approximated by a linear function. In other words, a logarithmic measure of tip-to-body impedance might be approximately linearly related to the thickness of the ice-layer. Thus a logarithmic measure of the normalized magnitude of impedance might be a useful indicator for ice-layer thickness.

In the second plot on the right side of FIG. 3 the output signal of a voltage divider structure is normalized by the input voltage. Trace 35 shows the result obtained for the tip-to-body impedance of electrode 23a in series with an ohmic reference resistor (not shown). For the depicted example the value of the ohmic resistor is twenty times the magnitude of the impedance obtained at body temperature. For this configuration the change of the output voltage with increasing ice-layer thickness is most pronounced for a medium thickness (approximately 1 mm for the shown example) and smaller for a smaller or higher thickness. Thus, such a parameter might be used when monitoring an ice formation at a certain target thickness is of interest.

By splitting the entire heat exchange surface into two structures, i.e. into the first electrode 23a and the cryo-applicator 53 high changes of resistivity displayed in FIG. 1 may be transformed into a high change of a local impedance measured by using the first electrode 23a. The magnitude of this change of impedance might be larger than two orders of magnitude. Due to this strong variation it might be of advantage in some applications to assess a properly defined impedance parameter as for example a logarithmic measure or the output of a voltage divider structure for monitoring the formation of ice. Thus, a properly selected impedance parameter might be displayed by a computer system for monitoring the progress of ice formation during a cryo-ablation and a melting of the ice-layer after termination of the treatment. However, also parameters not shown in the example might be used as for example simple magnitude or phase information of impedance or more elaborated combinations of resistive and capacitive components measured at multiple frequencies. Computer modelling might be applied for obtaining a particular parameter as for example the thickness of the ice layer estimated from measured impedance parameters. However, throughout this application it is assumed that the impedance parameter is defined in such a manner that it continuously increases with increasing size of the lesion i.e. with increasing the size of treatment region of the tissue 25.

In another embodiment the first electrode 23a and the cryo-applicator 53 might be electrically connected. Thus, they effectively form one common terminal. This might be achieved by an electronic circuit in an appropriate measurement and control device which is described below in more detail. Alternatively they might form one common electrode 23 with a single supply lead 22a which eases manufacturing. By electrically connecting the first electrode 23a and the cryo-applicator 53 the resulting tip-to-body impedance is more influenced by the blood flow surrounding the cryo portion 21 of the catheter device 20. In other words, the cryo-applicator 53 which is mainly in contact with the blood pool 24 is wired in parallel with the first electrode 23a which is mainly in contact with the tissue 25.

Trace 32 in FIG. 3 shows the tip-to-body impedance of the first electrode 23a being connected in parallel with (the electrode of) the cryo-applicator 53 as a function of the thickness of the ice layer. Again a semi-logarithmic plot is applied and data is normalized by the tip-to-body impedance at body temperature. It is noted that the changes of impedance are now somewhat reduced as ice formation in the blood flow might be less pronounced compared to ice formation in tissue. Therefore, this embodiment (with electrically connected first electrode 23a and cryo-applicator 53)

might be applied in particular if a coarse parameter for monitoring ice formation is sufficient.

Trace 36 shows the output of a voltage divider structure obtained for the common electrode consisting of the first electrode 23a and the electrode represented by the cryo-applicator 53. In this example the value of the used ohmic resistor is four times the magnitude of the impedance obtained before freezing.

For the treatment of cardiac arrhythmia the ablation might be performed in the atrial myocardium. In this case the target issue is a muscle with a typical thickness in the order of 1 to 3 mm. By designing the first electrode 23a in such a manner that it is mounted on a portion of the catheter tip 21 which is in contact with the target tissue during ablation and limiting the contact area of the first electrode 23a to be less than 5 mm2 or more particularly less than 3 mm2 the impedance might increase by more than two orders of magnitude (i.e. by more than a factor of 100) during ablation. Therefore, proper means are needed for measuring impedance over more than two orders of magnitude.

A person skilled in the art will readily understand that impedance measurements can also be used for assessing the wall contact of a catheter tip as it is taught by U.S. Pat. No. 5,673,704. When assessing wall contact before starting ablation or tissue necrosis after ablation the magnitude of the impedance will change typically less than a factor of two. Thus, here measurements must be sufficiently accurate to resolve changes in the order of a few percent and also the information displayed by an entire ablation system containing the cryo-ablation catheter must be designed for displaying these changes. Thus, if wall contact and ice formation should be assessed with one device it must be designed such that (a) small variations of impedance at body temperature can be accurately resolved and (b) strong variations during freezing can be properly resolved.

Figure 4:
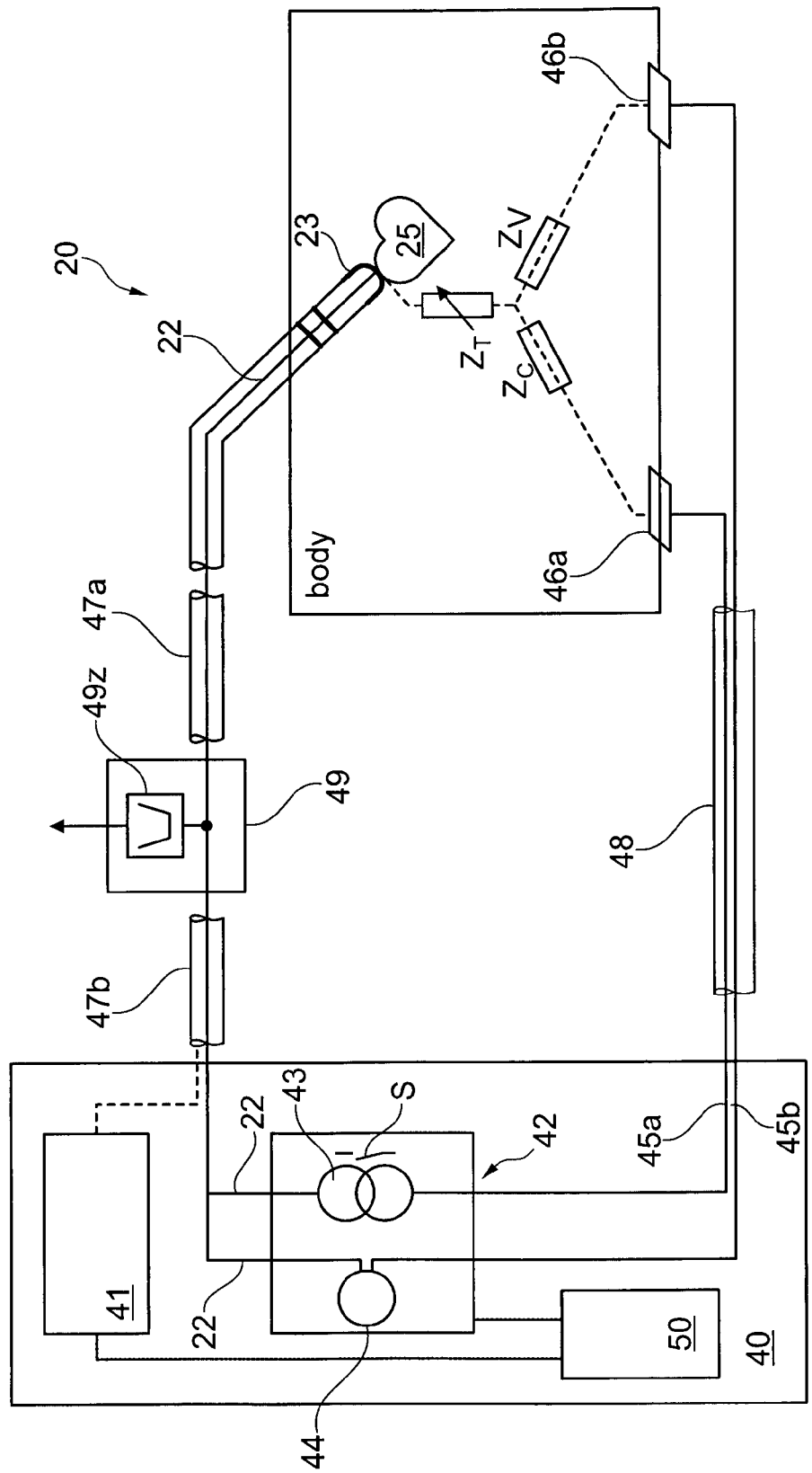
FIG. 4 shows an entire ablation system.

FIG. 4 shows an entire ablation system according to an embodiment of the invention. The ablation system comprises a so called cryo-ablation console 40. According to the exemplary embodiment described here the cryo-ablation console 40 hosts an ablation control unit 41 for controlling the ablation process. The ablation control unit 41 might involve not depicted control valves (refrigerant supply and draining), pressure sensors, a refrigerant flow rate sensor and instrumentation for measuring temperatures and pressures in the catheter or supply line 26. Further, the cryo-ablation console 40 hosts a monitoring unit 42 and a computing unit 50 which is bi-directionally connected with the ablation control unit 41 and the monitoring unit 42. The computing unit 50 controls the units 41 and 42 based on a feedback obtained from these two units 41, 42. The computing unit 50 may consist of a microcontroller board and/or a workstation. For an operation controller by a user, in particular a physician, not depicted input and output devices such as a keyboard, a mouse, button, a display, a monitor or a touchscreen are foreseen.

In the depicted embodiment the tip-to-body impedance ZT is used as a parameter for assessing wall contact and the progress of the ablation process. It is noted that the symbol for ZT in FIG. 4 contains an arrow indicating the expected strong variation of impedance during freezing as outlined in FIGS. 1 and 3.

The monitoring unit 42 contains (a) a stimulation unit 43 delivering alternating current of a chosen frequency and chosen amplitude and (b) a voltage sensor 44 sensing the output voltage essentially proportional to the tip-to-body impedance ZT. A switch S indicates that the stimulation unit 43 can be switched to multiple output levels for properly assessing the strong variations of impedance during freezing. This will be addressed below in more detail with reference to FIGS. 12 to 14. The voltage sensor 44 has a high input impedance and may measure the amplitude and the phase information of the output voltage. In one embodiment the stimulation unit 43 might be a current source. In yet another embodiment it might be voltage source with a voltage divider structure.

In the depicted embodiment three leads 22, 45a, and 45b are provided and are used for assessing the electrical tip-to-body impedance ZT between the first electrode 23 and the target tissue 25. Lead 22 connects the first electrode 23 with the monitoring unit 42. This lead 22 is guided within the cryo-ablation catheter 20 and its connection cables 47a and 47b to the cryo-ablation console 40.

The cryo-ablation catheter 20 is an elongated or longitudinal structure designed such that the catheter tip 21 containing the first electrode 23 can be properly positioned inside the heart. The connection cables 47a and 47b contain also multiple leads (not shown) for assessing catheter temperatures, pressures and for operating electronic circuits in the catheter (for example information about catheter type).

According to the exemplary embodiment described here not depicted additional leads for recording electrograms from the target tissue 25 are guided within the longitudinal structure and a split box 49 is used for connecting them to additional clinical recording systems (also not shown). A filter structure 49z (for example a band stop or notch filter) is used to reduce interference of the alternating current supplied by stimulation unit 43 with the additional clinical recording systems. A separate cable 48 is used for connecting the lead 45a of the stimulation unit 43 with an electrode 46a on the body surface (for example located on the back or the abdomen of a patient) and for connecting lead 45b of the voltage sensor 44 with another electrode 46b on the body surface (located spatially separated from 46a).

The impedance of electrodes 46a and 46b to the target tissue are named $Z_C$ (current) and $Z_V$ (voltage). Thus, a Y model of an equivalent circuit might be used for such a three lead measurement configuration. When applying a defined alternating current I via the stimulation unit 43 the voltage sensor 44 will essentially measure the complex product $I \times Z_T$ as the voltage drop on $Z_V$ is almost zero due to a high input impedance of the voltage sensor 44. Thus, the tip-to-body impedance $Z_T$ can be readily calculated and displayed by the cryo-console 20.

In one application this impedance might be used in a first step for controlling a contact (pressure) of the catheter tip 21 with the target tissue 25. For example a first value $Z_T$ will be recorded for the electrode 23 floating without a wall contact in the blood flow 24 of a vessel or a heart chamber. When establishing a contact with the wall of the target tissue 25 the impedance $Z_T$ will somewhat increase due to the poorer conductivity of tissue 25 compared to blood 24. Once tissue contact is confirmed by an increase of impedance a cryo-ablation procedure may be started and ice formation will occur in the target tissue 25 and also on the surface portion of the catheter tip 21 which is in contact with the blood flow 24. Thus, the tip-to-body impedance $Z_T$ will increase during ice-formation as described in FIG. 3. In FIG. 4 this increase of the tip-to-body impedance $Z_T$ is indicated by an arrow in the symbol of $Z_T$.

The output level of stimulation unit 43 might be adjusted during freezing in order to precisely measure the strong change of the tip-to-body impedance $Z_T$ during freezing. After termination of the freezing procedure by stopping refrigerant supply the tip-to-body impedance $Z_T$ will decrease again. Also here the output level of stimulation unit 43 might be properly adjusted. If the catheter tip 21 is kept in the same location as prior to freezing the tip-to-body impedance $Z_T$ might decrease to a value which is even smaller as a corresponding value before starting the ablation procedure. This may be based in the matter of fact that a cell destruction by ablation can increase the conductivity of the tissue 25. Thus, a proper monitoring of the tip-to-body impedance $Z_T$ may allow for providing a quantitative parameter being indicative for the progress of the ablation progress.

In an alternative embodiment also the return leads 45a and 45b are guided via the cable 48, via the split box 49 and via the cable 47b to the cryo-ablation console 40. In yet another embodiment the monitoring unit 42 might be a separate device not included in the cryo-ablation console 40. This separate device may contain also a computing unit with appropriate input/output devices.

In an alternative embodiment the electrodes 46a and 46b are combined to a single common return electrode 46 being connected via a combined return lead. In such an embodiment the tip-to-body impedance $Z_T$ is in series with the return impedance and only the sum of both values can be measured (two lead impedance configuration). This might provide a sufficient accuracy in some applications for example if the tip-to-body impedance $Z_T$ has a very high magnitude during freezing or if the magnitude of the return impedance is kept small for example by using a large area electrode.

In this respect it is mentioned that also four-lead impedance configurations which are known for example from U.S. Pat. No. 5,603,333 could be used. In some applications also such four-lead-configurations might be used for example by using a plurality of leads and corresponding electrodes arranged at a tubular body of the catheter device.

Figure 5:
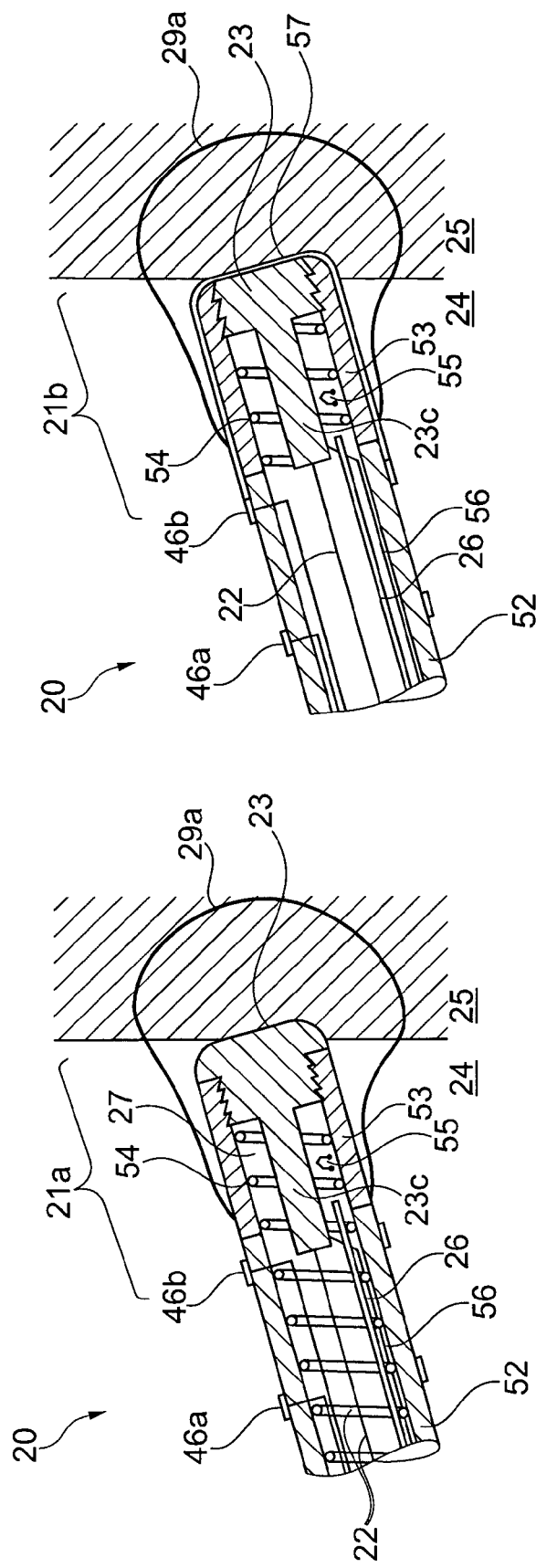
FIG. 5 shows two alternative embodiments for a catheter tip of a catheter device.

FIG. 5 shows two alternative embodiments for the catheter tip 21. These embodiments are denominated with reference numerals 21a and 21b. The catheter tip 21a uses electrodes 46a and 46b which are located proximally from the first electrode 23 at the longitudinal structure of the cryo-ablation catheter 20. Electrode 46a is connected by lead 45a to the stimulation unit 43 (see FIG. 4). Electrode 46b is connected by lead 45b to the voltage sensor 44 (see FIG. 4). In other words, instead of placing the electrodes 46a, 46b at the body surface as shown in FIG. 4, according to the embodiment described here the two electrodes 46a, 46b are located at the catheter with a proper spatial spacing with respect to each other. In the depicted embodiment electrode 46b is spatially located in between electrodes 23 and 46a along the axis of the catheter. All these electrodes 23, 46a, and 46b might be used not only for impedance measurements but also for recording signals close to the target tissue 25. The cable 48 (see FIG. 4) is not used in this embodiment as leads are now guided by the connection cables 47a and 47b.

In yet another embodiment the electrodes 46a and 46b are located on a separate diagnostic catheter advanced into the body and cable 48 is used for connecting these electrodes to the split box 49 depicted in FIG. 4.

The electrode 23 is a thermally and electrically conducting body. It is shaped such that most of its surface at the catheter tip 21a can be brought in contact with the tissue 25. Thus, the impedance measured by this configuration during freezing will mainly reflect tissue impedance similar as indicated by trace 31 in FIG. 3. For measuring temperature a sensor 55 (for example a thermocouple or thermistor) is located in the boiling chamber 27. The temperature sensor 55 might or might be not in thermal or electrical contact with the electrode 23.

For improving heat conduction from the boiling chamber 27 to the tissue under treatment 25 two measures are applied in the depicted embodiment:

(A) Firstly, the electrode 23 involves a protruding portion 23c at its proximal end which increases the contact surface of the electrode 23 with the cooling fluid within the boiling chamber 27. Thus, the heat transfer between the cooling fluid and the tissue 25 is increased. According to the exemplary embodiment described here also the cross section of the boiling chamber 27 is reduced by the protruding portion 23c. Thus, the thickness of the protruding portion 23c in combination with the diameters of (a) a tube like elongated catheter shaft 52, a tube of the applicator 53, and a support element 54 (for example a helix or a stent like structure) also defines the pressure in the boiling chamber 27 for a given refrigerant flow rate.

(B) Secondly, the distal catheter tubing i.e. the applicator 53 is made from a material which is thermally conducting but an electrical isolator. For example metallic particles might be included in a plastic matrix for increasing thermal conductivity while preserving electrical isolation. Also this contributes to a heat transfer between the boiling chamber 27 and the tissue 25 in the region of the catheter tip 21. At its proximal end the cryo-applicator 53 is connected (for example welded or glued) to the elongated catheter shaft 52. This shaft 52 maybe composed by braided tubing.

According to the exemplary embodiment described here a pull wire 56 is foreseen for making the catheter tip 21a steerable. The pull wire 56 might be connected to the electrode 23 or to the support element 54. It is mentioned that similar as depicted in FIG. 2 the heat transfer interface is composed by two structures: The electrode 23 and a thermally conducting tube respectively the cryo-applicator 53. This allows for a reduction of the surface of electrode 23. Thus, measurements performed by the catheter tip 21a of the catheter device 20 are sensitive for local changes of tissue resistance.

In yet another embodiment only one common return (second) electrode 46 and one common lead connected thereto might be used. In other words, the electrodes 46a and 46b may be combined into one single electrode located at a portion of the catheter device 20, which portion is proximal from the catheter tip 21a on the body surface (two lead impedance). It is noted that for such a common return path the tip-to-body impedance $Z_T$ is now in series with one return impedance $Z_R$ and only the sum $Z_T+Z_R$ can be measured (two lead configuration). Referring to FIG. 3 a strong increase of $Z_T$ is expected during freezing when the catheter device 20 is located such that the electrode 23 is in contact with the tissue 25. Thus, for monitoring ice-formation proper design of the common return electrode 46 (for example a sufficiently large electrode surface) might ensure that the influence of $Z_R$ is almost negligible ($Z_R$ is much smaller compared to $Z_T$) and a sufficient accuracy might be obtained for many types of applications.

For the catheter tip 21b the outer surface of the first electrode 23 is coated by a thermally conducting but not electrically conducting layer 57. In other words the ohmic conductivity for a direct current through this layer 57 is poor and substantially corresponds to that of an electrical isolator. For example a plastic membrane or thin plastic tubing might be used for forming the layer 57. In this embodiment the electrode 23 and the layer 57 form a capacity (i.e. an electrical admittance conducting alternating current) to the tissue 25 or to the blood pool 24. It is noted that also in this embodiment the heat transfer is accomplished by the two structures (a) cryo-applicator 53 and (b) first electrode 23 while electric conduction to the tissue 25 is obtained indirectly via capacitive effects.

In some embodiments the support element 54 may be electrically conducting and in direct electrical contact with the electrode 23 and/or with the lead 22. In such an embodiment also the support element 54 contributes to an electrical conduction by admittance. In some embodiments the support element 54 may completely fulfill the function of the electrode 23 for assessing electrical impedance. Thus, only one common structure might be used for combining mechanical function of the support element 54 and the electrode 23.

For the catheter tip 21*b* the electrical impedance from the electrode 23 and/or from the support element 54 to the tissue under treatment 25 might significantly alter when the catheter device 20 gets leaky. In particular, a phase shift might be detected if blood, body or flushing liquid enters the inside the catheter tip 21. Thus, the electrical impedance assessed by the monitoring unit 42 might be used also by a safety system of the cryo-ablation console 40 for detecting leakage.

Figure 6:
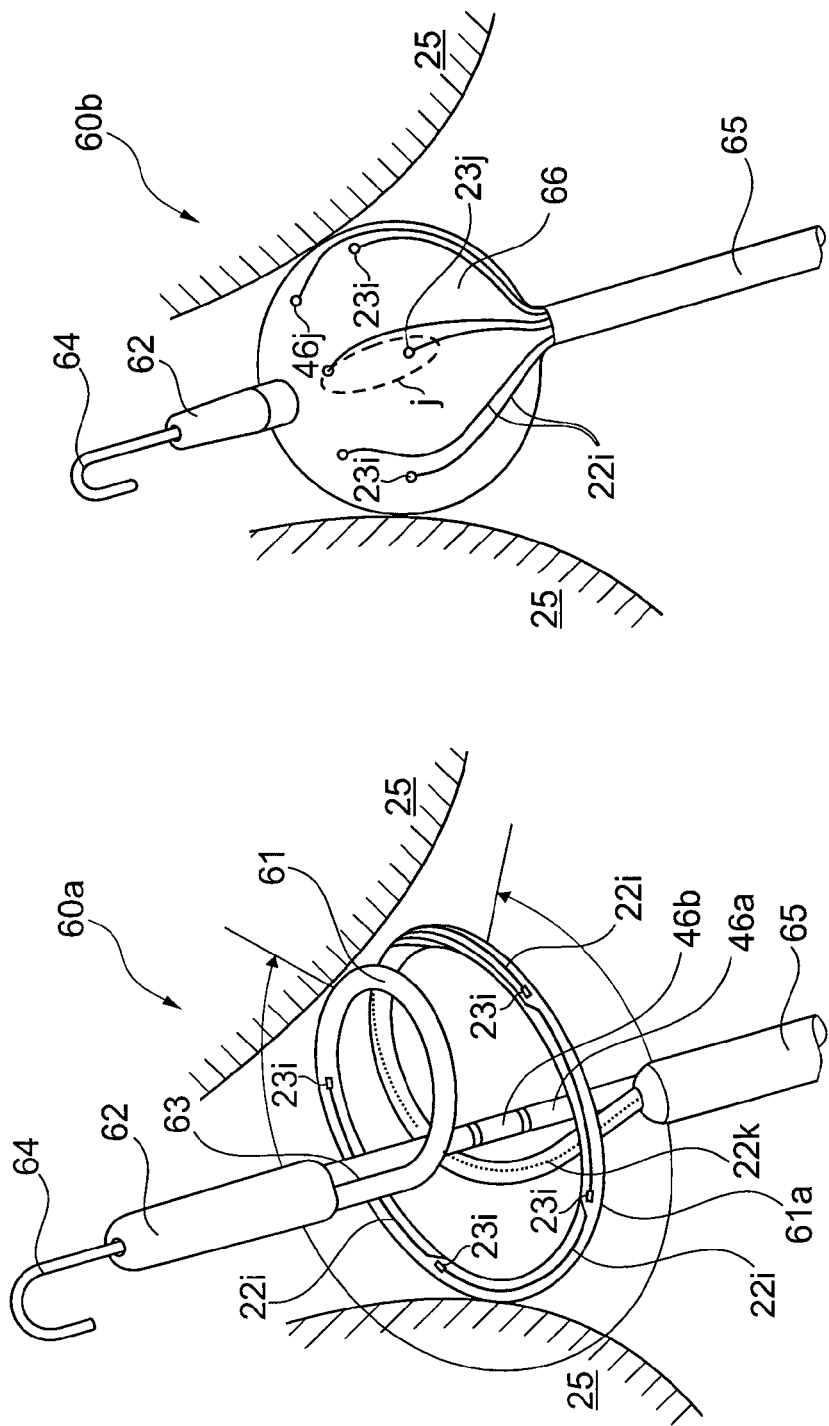
FIG. 6 shows two further embodiments 60*a* and 60*b* for an elongated cryo-ablation catheter.

FIG. 6 shows two further embodiments 60*a* and 60*b* for an elongated cryo-ablation catheter. Both cryo-ablation catheters 60*a* and 60*b* are configured for creating an essentially circular lesion around the orifice of a vessel or tubular structure of a body under treatment. For example the tubular structure might be a vein branching off from the atria of the heart or a renal artery. Thus, these configurations produce an elongated lesion with a long extension in at least one direction.

The cryo-ablation catheter 60*a* is a loop type catheter with a cryo-applicator tubing 61. An active portion 61*a* of the cryo-applicator tubing 61 is cooled during ablation by applying a cooling fluid inside the active portion 61*a* of the sealed cryo-applicator tubing 61. For a placement around the orifice a distal member 62 is advanced into the vein and a positioning catheter 63 may host a guide wire 64 which is used for advancing the entire catheter device in an essentially stretched configuration (not shown). By applying a proper mechanical tensile force the catheter device is transformed into a loop shape and pressed around the target tissue 25.

For monitoring wall contact, freezing progress and ablation outcome a plurality of electrodes 23*i* is located at the outer surface of the cryo-applicator tubing 61 with a proper inter-electrode spacing in azimuthal direction. These electrodes 23*i* can be used for individually measuring impedances at each electrode 23*i*. For example a multiplexer structure might be used in order to sequentially measure impedance with a multiple number of electrodes 23*i* (further details are presented below with reference to FIG. 14). In such a configuration multiple leads 22*i* are guided from the cryo-applicator 61 to the monitoring unit 42. In the shown embodiment the electrodes 23*i* and the leads 22*i* are guided at the outer surface of the cryo-applicator tubing 61. This can be accomplished for example by using stretchable elastomer and/or nano-electronic composites. The dotted line 22*k* indicates that in the shown drawing leads are guided on the backside of the cryo-applicator tubing 61 and are, thus, not visible.

The leads 22*i* might be coved by an electrically isolating layer for achieving electrical isolation to the body. Proximally from the insertion of the cryo-applicator tubing 61 into an elongated catheter shaft 65 they might be wired to leads passing inside the shaft 65 towards the a catheter handle (not shown).

The electrodes 23*i* are placed onto the cryo-applicator tubing 61 in such a manner that they are directed towards the tissue 25 during the treatment and the areas of the electrodes 23*i* are sufficiently small for being mainly in contact with the tissue 25. It is noted that the outer cryo-applicator tubing 61 in the active portion 61*a* has essentially the same function as the cryo-applicator 53 shown in FIG. 5. In combination with the electrodes 23*i* the active portion 61*a* contributes to a heat transfer to respectively from the tissue 25 under treatment.

In yet another embodiment electrodes 23*i* might be ring-electrodes at the outer-surface of the cryo-applicator tubing 61 and the leads 22*i* might be guided inside the tubing 61. In another embodiment leads 22*i* and electrodes 23*i* might be guided inside the cryo-applicator tubing 61. In this case an impedance measurement might be achieved via capacitive coupling to the tissue 25 under treatment similar as described above with reference to FIG. 5.

Further, also support elements or structures within the inside of the cryo-applicator tubing 61 might be used for a capacitive coupling. Metallic particles added to a plastic matrix of the cryo-applicator tubing 61 might provide a double function: increasing of thermal conduction to the tissue 25 and increasing electrical admittance from the respective electrode 23*i* to the tissue 25.

In the elongated cryo-ablation catheter 60*a* depicted on the left side of FIG. 6 two return electrodes 46*a* and 46*b* formed or provided at the positioning catheter 63 are used for providing the electric return path for an impedance measurement. Alternatively, the two return electrodes 46*a* and 46*b* might be placed in another location at the catheter device as for example the distal member 62 or the elongated catheter shaft 65. In yet another embodiment one combined electrode might be used as described above with reference to FIG. 5. In another embodiment the two return electrodes 46*a* and 46*b* might be placed at the surface of a body under treatment as described above with reference to FIG. 4. In another embodiment the cryo-applicator tubing 61 might have an essentially linear structure for creating an essentially linear lesion in a target tissue 25. In yet another embodiment the cryo-applicator tubing 61 might have an essentially helical shape for creating an essentially helical lesion in a target tissue.

The elongated cryo-ablation catheter 60*b* shown on the right side of FIG. 6 applies a balloon like applicator structure 66 for creating a lesion around an orifice of a vessel or ring like structure. In this configuration the elongated cryo-ablation catheter 60*b* is introduced into a body under treatment with the balloon 66 deflated. A distal member 62 and a positioning catheter 63 inside the distal member 62 are used to advance the entire cryo-ablation catheter 60*b* over a guide wire 64. When being sufficiently close to the target tissue 25 the balloon 66 is inflated and advanced against the target tissue 25. Multiple electrodes 23*i* might be located at the balloon 66 and multiple impedance parameters displayed for individual configurations might be used for monitoring the respective wall contact during placement of the catheter 60*b*. Stretchable elastomer or nano-electronic composites may be used for shaping these electrodes 23*i* and their corresponding leads 22*i*. For the shown example multiple common return electrodes 46*i* (i.e. measurement of multiple two lead impedances) are located in the distal area of the balloon like applicator structure 66.

In this configuration an ice-formation in a segment j related to an individual electrode pair 23*j* and 46*j* may be assessed. The electrodes 23*i* are placed onto the balloon 66 in such a manner that they are directed towards the tissue 25 during the treatment and their area is sufficiently small for being mainly in contact with the tissue 25 under treatment. It is noted that the cooled surface of the balloon 66 has essentially the same function as the cryo-applicator 53 shown in FIG. 5. In combination with electrodes 23*i* the surface of balloon 66 contributes to a heat transfer to respectively from the tissue 25 under treatment.

In another embodiment the return electrodes might be located at the catheter tip, the shaft, the proximal balloon or the body surface. They might also be combined in one single lead to measure multiple two lead impedances for each electrode. In another embodiment the electrodes 23*i* might be located inside the balloon 66 and the impedances might be measured by a capacitive coupling. In such a configuration a measured impedance value might be also used for leakage detection. In yet another embodiment the balloon 66 might be composed by two separate membranes one inside the other but in tight contact for increasing functional safety if one of the two membranes gets leaky. In such an embodiment the electrodes 23*i* might be located between the two membranes for detecting leakage or rupture of membranes.

The two elongated cryo-ablation catheters 60*a* and 60*b* may or may not comprise a pull wire for steering. Alternatively or additionally to a steering mechanism a steerable sheath as known by those skilled in the art might be used for steering the cryo-ablation catheters 60*a*, 60*b*.

Figure 7:
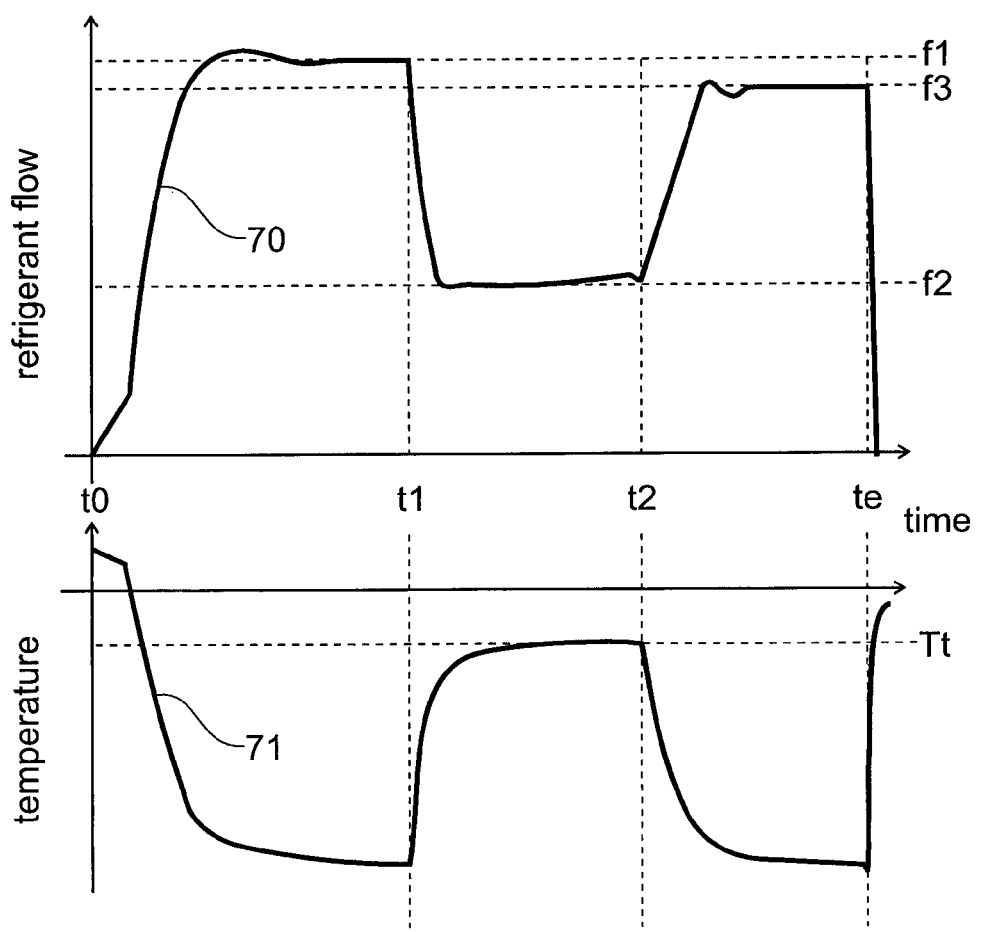
FIG. 7 shows a diagram illustrating an example of a cryo-ablation cooling cycle.

FIG. 7 shows a diagram illustrating an example of a cryo-ablation cooling cycle. In the upper part a refrigerant or cooling medium flow rate 70 is plotted over time. In the lower part of FIG. 7 the time dependent temperature 71 resulting from the time dependent cooling medium flow rate 70 is plotted over time.

Referring to trace 70 at time point t0 a cryo-ablation procedure is started and after a transient phase an approximately steady flow rate f1 (i.e. essentially constant cooling power) is obtained. At a time point t1 the flow rate might be reduced (modulated) by the ablation control unit 41 of the cryo-ablation console 40 shown in FIG. 4 for example by reducing the supply pressure at a refrigerant supply line. Time point t1 may be predefined or may be the time when a target temperature is obtained. A predefined time frame might be between 20 seconds and 200 seconds. The flow rate may be controlled to approach a second flow rate f2. At a preset time point t2 the ablation control unit 41 might increase the flow rate again to a third flow rate f3. The time point t2 might be chosen such that the interval between t1 and t2 lasts for example more than 10 seconds but less than 100 seconds. The flow rate f3 may be identical to the flow rate f1 in certain configurations and close to or identical to the nominal flow rate of the catheter. At an end time point to the freezing is terminated and the catheter is drained. In some configurations multiple steps of flow rate modulation may be foreseen during one ablation step.

Similar to freeze-thaw-freeze phases such a modulation of refrigerant flow will induce temporal (and spatial) temperature gradients in the target tissue. These temporal gradients may contribute to an improved therapeutic effect or increased spatial extension of the resulting lesion. A proper choice of the flow rates f1, f2 or f3 might ensure that the catheter tip remains frozen at the location where ablation was started throughout the entire ablation process. This might reduce the need for uncomfortable and error prone multiple catheter manipulations. Furthermore, this might contribute to avoiding displacements of the catheter tip during an ablation procedure as it might occur for a freeze-thaw-freeze cycle with a complete thawing.

The trace 71 show an exemplary time dependent temperature course at the catheter tip, which course results from the course of the flow rate described with trace 70. A properly selected threshold temperature Tt might be used for ensuring that the catheter tip remains frozen at the lowest flow rate value during the modulation of the freeze-thaw-freeze cycle. The computing unit 50 illustrated in FIG. 4 may be adapted for automatically controlling the ablation control unit 41 in order to ensure that the temperature remains below the threshold between first reduction of flow rate t1 and the end of reduced cooling power at t2.

In another embodiment the flow rate might be continuously increased in steps. For example, this might be applied for controlling catheter location at a low not lethal cooling rate before increasing cooling power to a level sufficient to create permanent lesion formation (cryo-mapping).

Figure 8:
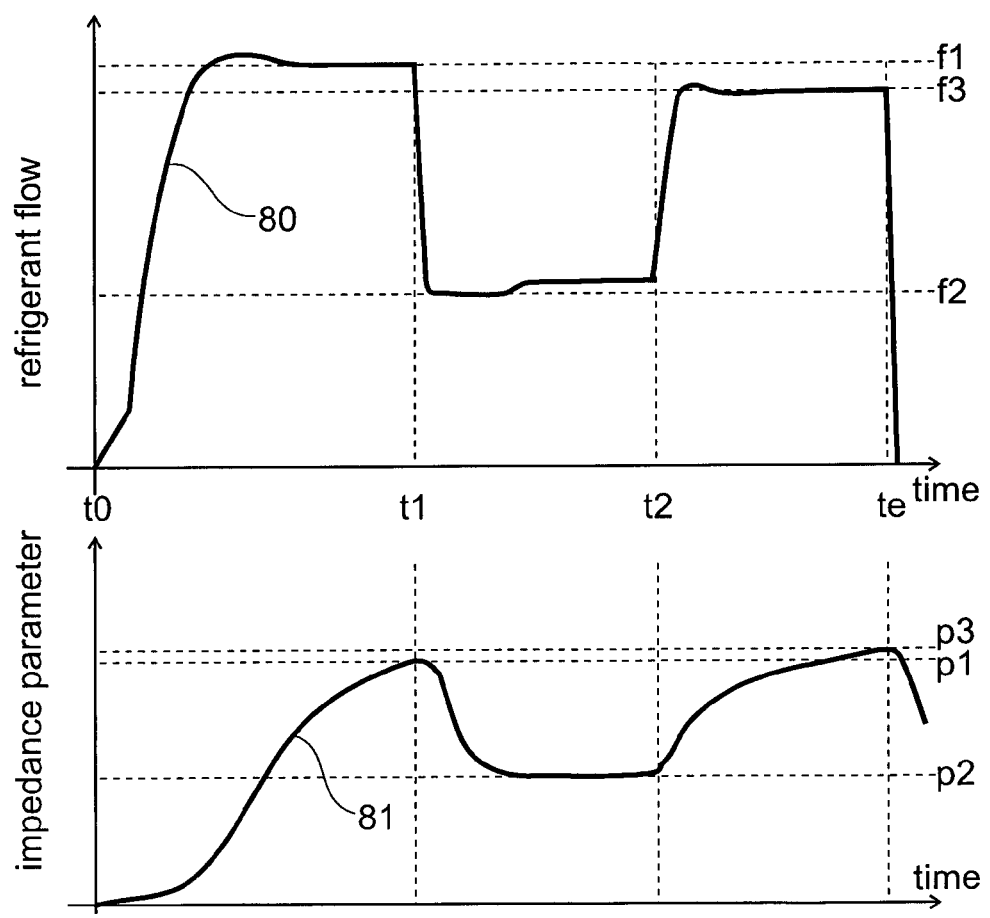
FIG. 8 shows diagram depicting a time modulated flow rate of a refrigerant and the resulting time modulation of the impedance value.

FIG. 8 shows a diagram depicting with a trace 80 a time modulated flow rate of a cooling medium respectively refrigerant and with a trace 81 the resulting time modulation of the impedance value measured with the catheter device described in this document.

First, upon starting freezing an ice formation starts and the thickness of the resulting ice layer may increase over time. The impedance value might indicate the size of the frozen region progressing with time. At time t1 modulation might be started when a certain impedance value p1 is reached. However, in certain configurations t1 might be a preset value or an upper timer limit might be used for t1. Upon reducing the refrigerant flow rate the correspondingly reduced thermal load will cause a melting in the border zone 29*a* of the frozen tissue region (see FIG. 2) and the impedance value will decrease again. In the shown example the computing unit 50 is adapted for controlling the refrigerant flow rate such that the impedance value does not decrease below a threshold p2. In other words, at the time point t2 the set point of the refrigerant flow rate is chosen to be f2 but this set point might be controlled by a target value of p2 for the impedance. A cascade like control structure might be used for obtaining this behavior. After a preset time interval the ablation control unit 41 might increase the flow rate again to a value f3.

Freezing might be stopped after a preset time or if a third threshold impedance value p3 is reached.

Without being bound to a specific theory it should be clear that an impedance value might better reflect the spatial extension of an ice-formation within the tissue compared to the temperature value of the catheter tip or the temperature within the boiling chamber temperature which are also influenced by the boiling cooling fluid respectively refrigerant. Thus, the trace 71 in FIG. 7 and the trace 81 in FIG. 8 represent an information content which might be correlated to some degree but each trace contains information which is independent from the other trace. Thus, in some embodiments a combination of temperature and impedance values might be used for controlling a precise modulation of a freezing procedure.

When operating cryo-ablation catheters at different refrigerant flow rates this might impact the pressure within the boiling chamber at the catheter tip. For example, the cryo-ablation catheter might be designed to operate at a nominal boiling chamber pressure for a given nominal flow/pressure within the refrigerant supply lines and a given nominal vacuum level within the refrigerant draining lines. Typically, this nominal boiling chamber pressure will be at a relatively low pressure level for safety issues and for keeping the boiling temperatures low. When operating the cryo-ablation catheter at a flow rate below its nominal flow rate the boiling chamber pressure might also further decrease. Here, depending on the design of the cryo-ablation system comprising the cryo-ablation catheter, proper measures have to be taken in order to avoid that the pressure drops below the triple point pressure of the refrigerant. Below the triple point pressure of the liquid phase the refrigerant will transform into a mixture of a gaseous and a solid state medium. In such a situation the stable operation of the cryo-ablation catheter becomes difficult.

Figure 9:
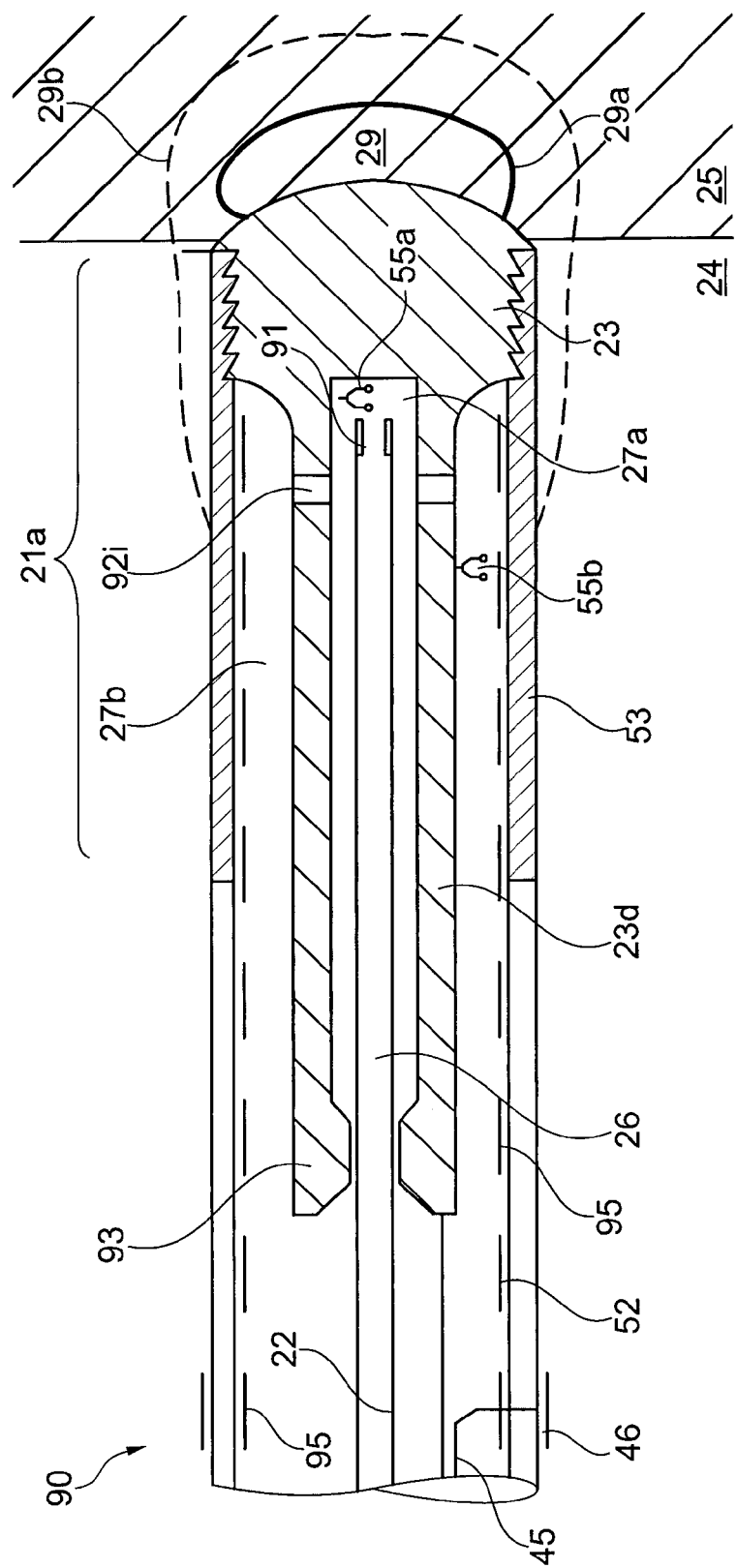
FIG. 9 shows a distal member of a cryo-ablation catheter having a split boiling chamber.

FIG. 9 shows, in accordance with further embodiment of the invention, a distal member of a cryo-ablation catheter 90 which uses a split boiling chamber design for operating the catheter 90 at a nominal refrigerant flow rate and at a reduced refrigerant flow rate. In the depicted embodiment the (first) electrode 23 is a thermally and electrically conducting body located at the catheter tip 21a of the cryo-ablation catheter 90. It is noted that the structure of the electrode 23 is designed to fulfill multiple purposes including inter alia a proper heat transfer.

At the proximal end of the (first) electrode 23 a distal member 23d is foreseen. This distal member 23d contains an inner cavity forming an inner boiling chamber 27a. The refrigerant supply line 26 is guided into that inner boiling chamber 27a. At an exit point 91 the refrigerant delivered along the supply line 26 enters the inner boiling chamber 27a. From this inner boiling chamber 27a the refrigerant is guided across one or more micro-holes 92i to the outer boiling chamber 27b. A sealing structure 93 at the proximal end of the elongated member 23d limits the direct exit of refrigerant in direction towards the elongated catheter shaft 52. A thermally conducting tubing of an cryo-applicator 53 is foreseen as an additional heat transfer structure towards and from the body in addition to the structure of the electrode 23. A helical or stent like support structure 95 might be used for preventing the tubing of the cryo-applicator 53 from kinking.

The dimensions of the double boiling chamber arrangement are chosen such that at a high flow rate (essentially the nominal flow of the cryo-ablation catheter) the pressure in the outer boiling chamber 27b is above the triple point pressure of the refrigerant. In the inner boiling chamber 27a the pressure is higher compared to the pressure within the outer boiling chamber 27b. This means in turn, that the boiling point of the refrigerant is lower in the outer boiling chamber 27b compared to the inner boiling chamber 27a. Thus, the refrigerant might boil out mainly in the outer boiling chamber 27b. In other words, the boiling chamber design shown in FIG. 9 provides a sufficient heat transfer from the outer boiling chamber 27b to the tissue 25 under treatment for boiling out the refrigerant in the outer boiling chamber 27b. This is achieved by thermally connecting a volume of the lowest boiling temperature with the tissue 25 via the outer tubing of the cryo-applicator 53 and the electrode 23 in combination with the distal member 23d.

It is noted that that the function of the tubing of the cryo-applicator 53 is essentially the same as in the embodiment shown in FIG. 5. In combination with the electrode 23 the surface of the cryo-applicator 53 contributes to a heat transfer to the body. Thus, the electrode 23 can be designed sufficiently small for recording local impedance values at the catheter tip 21a.

When reducing the refrigerant flow rate to a reduced level, the pressure and the boiling point will decrease in both boiling chambers 27a, 27b. Due to the decrease of the flow rate also the supplied cooling power is reduced. This means in other words that a smaller amount of heat flow might be sufficient for boiling out the refrigerant. In such a situation the refrigerant might mainly boil out in the inner boiling chamber 27a as the elongated distal member 23d provides a sufficient heat transfer to the tissue 25 for essentially boiling out the refrigerant supplied at a reduced flow rate. In the outer boiling chamber 27b the boiling chamber pressure might now drop below the triple point pressure. However, as the refrigerant essentially boils out in the inner boiling chamber 27a the refrigerant entering the outer boiling chamber 27b will be (almost completely) in its gaseous phase. Thus, no significant amount of refrigerant may transform into the solid state and the cryo-ablation catheter can be operated at a reduced refrigerant flow rate.

At a high flow rate the cooling power is also high and the thickness of the ice-layer formed in the body is relatively large and an extended border zone 29b develops. In FIG. 9 this extended border zone 29b is indicated by the hatched line 29b. At a reduced refrigerant flow rate also the cooling power is reduced and the ice-layer is smaller but sufficiently larger to keep the cry-ablation catheter 90 fixedly frozen to the frozen tissue region 29 being spatially defined by the border zone 29a. Combining this behavior with the observations made in FIG. 3 and FIG. 8 a high impedance value can be achieved when freezing at a high flow rate. When freezing at a lower flow rate the impedance value might drop to a lower value. This lower value is between its maximal value at high flow rate and its value at body temperature. The flow of the refrigerant might be controlled in such a manner that a chosen target value for the impedance is achieved which ensures that the catheter tip 21a remains frozen to the tissue 25.

Using for example nitrous oxide as a refrigerant the triple point pressure is an absolute pressure of 878 mbar. When using tubing structures as a cryo-applicator 53 it is of advantage to keep the boiling chamber pressure relatively low for safety reasons. Thus, the outer boiling chamber 27b might be designed to operate at a nominal refrigerant flow rate in a nominal absolute pressure range of 950 mbar to 1250 mbar while the pressure in the inner boiling chamber 27a is at least 500 mbar higher as in the outer boiling chamber 27b.

Thus, temperatures between −85° C. and −90° C. might be obtained in the outer boiling chamber 27b at a refrigerant flow rate being 80% to 120% of the nominal flow rate. At a reduced flow rate the flow might be decreased to a level of 35% to 70% of the nominal flow rate. The nominal flow rate for cooling a catheter tip with an outer diameter of 7 Fr (=7 French Size in the so called French Catheter Scale), which corresponds to 2.33 mm, might be in the order of 0.075 to 0.115 g/s. The nominal flow rate will scale with the size of the catheter tip 21a while the pressure levels do not scale with the size of the catheter tip 21a.

At least one temperature sensor (for example a thermistor or a thermocouple) might be foreseen in order to assess at least one temperature at the catheter tip 21a. For example a temperature sensor thermally connected (for example soldered, laser welded or glued) to the electrode 23 might be used to measure the temperature at the interface of the catheter tip 21a to the tissue 25 under treatment. Alternatively or additionally, temperatures might be measured in the boiling chambers 27a, 27b of the cryo-ablation catheter 90 by isolating temperature sensors from contact to other structures as it is indicated by the temperature sensors 55a and 55b. In addition, the electrode 23 might be used for measuring bio-potentials from the target tissue 25 or an impedance value during freezing. The values of some or all of these parameters (temperature, bio-potential and/or impedance) might be used for monitoring and/or controlling the ablation process.

In one embodiment a pull wire might be connected to the electrode 23 and/or the support structure 95 in order to provide a steering mechanism to the catheter tip 21a. Additionally, an (second) electrode 46 together with a corresponding return lead 45 might be foreseen at the cryo-ablation catheter 90. It might be used (a) for measuring bio-potentials or (b) as a return electrode for impedance measurements.

Figure 10:
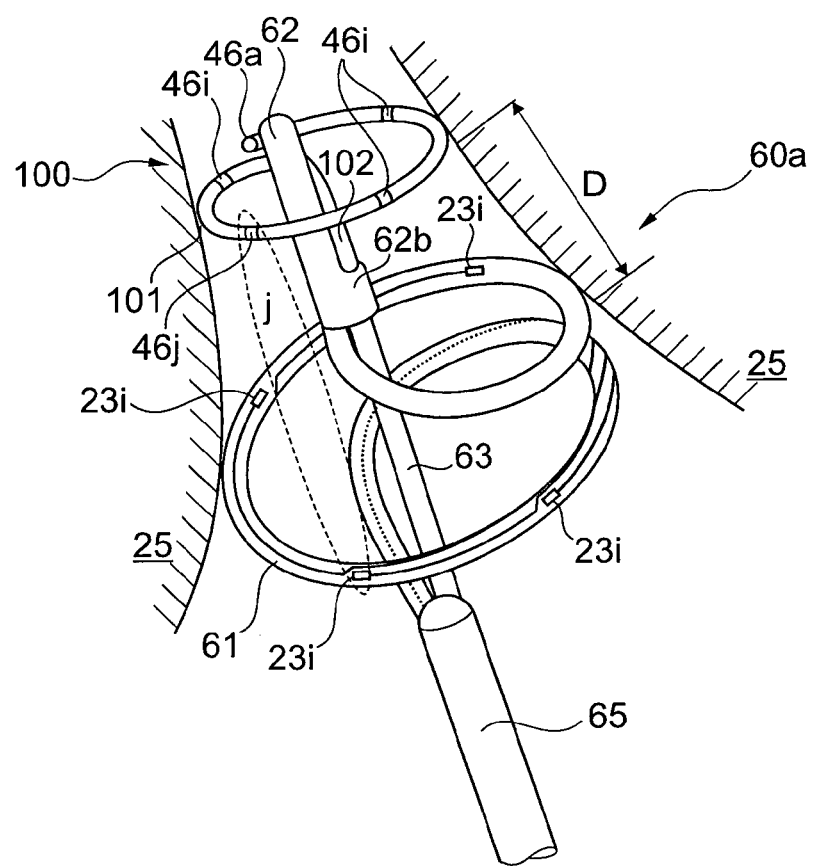
FIG. 10 shows a cryo-ablation catheter being provided with a diagnostic device

FIG. 10 shows a cryo-ablation catheter 60 being provided with a diagnostic device 100 which has been advanced through the common inner lumen of a positioning catheter 63 and a proximal portion 62b of the distal member 62. Similar as the embodiment shown in FIG. 6, the diagnostic device 100 may be used for positioning the helically shaped elongated cryo-ablation catheter 60a around the orifice of a vessel. Thus, an elongated shaft 102 of the diagnostic device 100 is made from a material that is sufficiently stiff and flexible to serve as a positioning tool for the elongated cryo-ablation catheter 60a. However, the elongated shaft 102 contains an inner lumen for guiding leads from a not depicted handle to a distal loop portion 101. Braided tubing or metal tubes for example made from stainless steel or Nitinol might be used for realizing at least the distal loop portion 101. A bending stiffness of the shaft 102 might be between 50 and 3000 Nmm$^2$ or more particularly between 150 and 1000 Nmm$^2$.

Additionally, the rotational stiffness of the shaft 102 is sufficiently high for allowing for rotating the diagnostic device 100 relative to the cryo-ablation catheter 60a around their common longitudinal axis. For the shown embodiment this distal portion of the diagnostic device 100 has the shape of a loop. A shape memory component (for example Nitinol) might be used inside the diagnostic device 100 for creating this shape. When rotating the diagnostic device 100 relative to the cryo-ablation catheter 60a a preferred direction of rotation might be defined by the geometry of the loop as might be indicated for the operator at a handle of the diagnostic device 100.

The shaft 102 and the distal loop portion 101 of the diagnostic device 100 are constructed with a sufficiently small dimension (e.g. diameter) that it can be advanced across the inner lumen of the cryo-ablation catheter 60a. In one embodiment this dimension is smaller than 1.83 mm or more particularly smaller than 1.33 mm.

This loop shaped distal portion 101 of the diagnostic device 100 might be located at a portion of the cardiac tissue between the venous ostium (i.e. the boarder of venous tissue and myocardium). Thus, the diameter of the distal loop portion 101 is smaller than the diameter of the loop of the cryo-applicator tubing 61. In the shown embodiment the tip of the cryo-ablation catheter 60a is properly shaped such that the distal member 62 provides a guiding essentially parallel to the axis of the vessel. The proximal portion 62b is shaped such that diagnostic device 100 extents for the tip at a location which has a small distance from the plane of the loop of the ablation cryo-applicator tubing 61. In other words, the geometry of the cryo-applicator tubing 61 is designed such that the distal loop portion 101 can be placed close to the loop of the cryo-applicator tubing 61. For example, for the shown configuration the axial distance D from the loop plane of the end of the diagnostic device 100 to the plane of the loop of the cryo-applicator tubing 61 is smaller than 3 cm and more particularly smaller than 2 cm.

In one embodiment a sufficiently small distance D might be achieved by designing the distal member 62 in such a manner that it is realized predominantly by the proximal portion 62b.

A set of electrodes 46i is located on the loop of the diagnostic device 100. These electrodes 46i might be used for multiple purposes. For example they can be used for recording electrograms inside the portion of tissue 25 to ablated by the cryo-applicator tubing 61. This might be helpful in order to access the outcome of ablation by verifying that no bio-electric pulses are conducted across the lesion created by the cryo-applicator tubing 61 during treatment. Alternatively, the electrodes 46i can be used for pacing the tissue 25 inside the loop of the cryo-applicator tubing 61. Again this can be used for verification of the outcome of ablation by ensuring that no bio-electric pulses propagate across the lesion as can be verified by using simultaneous ECG recordings. Furthermore, the electrodes 43i can be used as return path electrodes for an assessment of impedance values.

In one application prior to freezing the user might rotate the diagnostic device 100 relative to the cryo-ablation catheter 60a such that respectively two electrodes 46j and 23j form a pair j of neighboring electrodes in the same azimuthal segment (similar to the pair of electrodes 46j and 23j shown on the right side of FIG. 6).

In such a configuration the two-lead impedance recorded for the electrode pair 23j and 46j might accurately reflect ice formation in this azimuthal segment. An alignment of the electrodes 46j and 23j can be confirmed for example visually by imaging techniques as for example X-ray. Alternatively or additionally, such an alignment can be confirmed by multiple two-lead impedance recordings for example from one electrode 23j to all leads 46$_i$. Electrode pairs located near two each other will tend to display lower impedance compared to distant locations. The monitoring unit 42 shown in FIG. 4 might be adopted to perform such a type of multiple measurement e.g. by using multiplexer structures. A software of the computing unit 50 may be adopted to identify geometrically neighboring electrodes 23i and 46i as a pair j. Additionally, impedance values might be analyzed for estimating the distance D between the loop plane of the diagnostic device 100 and the loop plane of the cryo-applicator tubing 61.

In another application the return leads for all electrodes 46i might be wired in parallel for an impedance measurement. In other words, all such leads together form one common terminal. In one embodiment this common terminal might be used as a voltage sensing lead 45b as depicted in FIG. 4. By using one common terminal 45b the impedance $Z_V$ might display a low value. Thus, the Y-model equivalent circuit depicted in FIG. 4 can be interpreted in this configuration as follows:

For each electrode 23i an Y-model can be applied containing an applicator impedance $Z_i$ (electrode 23$_i$), a voltage return impedance (all electrodes 46i in parallel), and a current return impedance (second electrode 46a). For the depicted embodiment this electrode 46a is located at the distal end of the distal loop portion 101. However, this electrode 46a might also be located for example at the shaft 102, at the positioning catheter 63, at the catheter tip of the cryo-ablation catheter 60a or at a second not depicted diagnostic catheter. In this configuration the voltage return impedance (i.e. the magnitude of the complex impedance) might be smaller than the magnitude of the impedances $Z_i$. Thus, the influence of this impedance on the measured impedance value might be small in this configuration. Thus, the computed impedance values might mainly reflect tissue or blood conductivity in the vicinity of each electrode $23_j$.

In yet another embodiment one or a plurality of electrodes 46i might be used as a (common) current return electrode 46a and the remaining electrodes 46i might be used as a common voltage return electrode 46b as illustrated in FIG. 4.

In yet another embodiment all electrodes 46i together form one common return electrode for measuring a plurality of two-lead impedances for each electrode 23i. Wiring all electrodes 46i in parallel the magnitude of the return impedance might be small. Thus, in such an embodiment the accuracy of two-lead impedance measurements might be comparable accurate to more complex three lead impedance measurements.

Figure 11B:
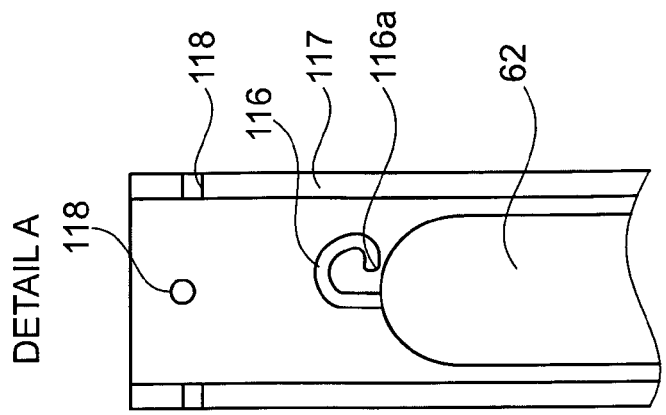
FIG. 11B shows a distal end portion of the diagnostic devices shown in FIG. 11A.
Figure 11A:
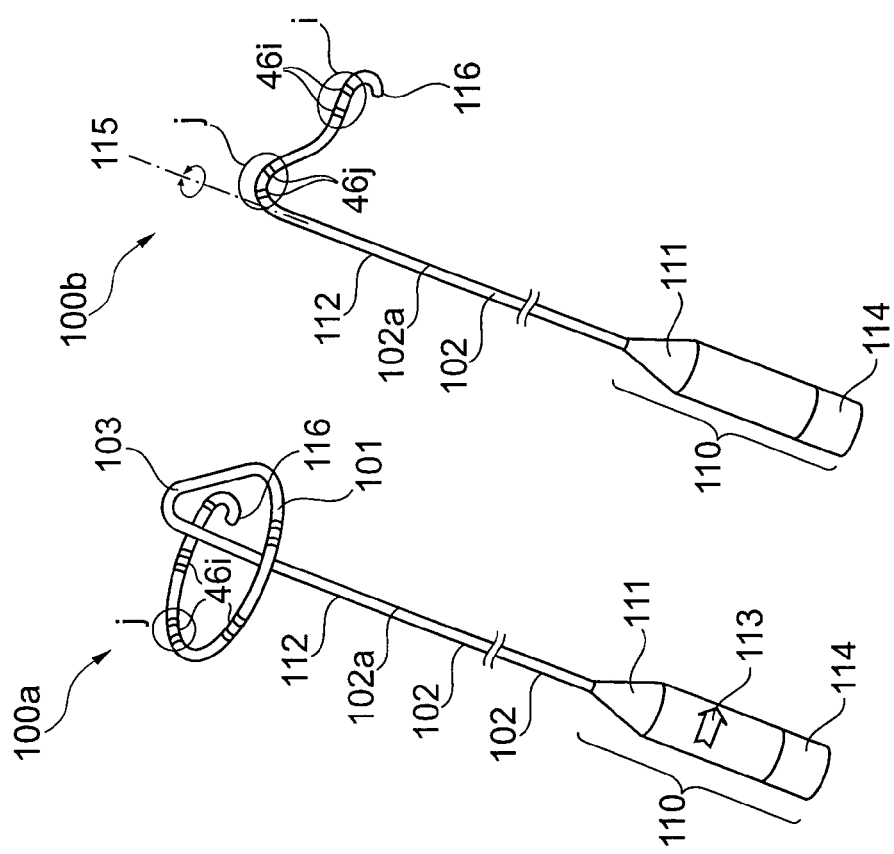
FIG. 11A shows two alternative embodiments for diagnostic device.

FIG. 11A shows two alternative embodiments 100a and 100b for realizing an elongated diagnostic device 100. Both diagnostic devices 100a and 100b might be used in combination with the cryo-ablation catheter 60a and 60b as shown in FIG. 6. For the sake of clarity, in FIG. 11A only the diagnostic devices itself are shown. When combining the device diagnostic device 100a or 100b with the cryo-ablation catheter 60a or 60b the diagnostic device 100a or 100b simply replaces the guide wire 64 depicted in FIG. 6, which guide wire 64 is advanced across an inner lumen of the cryo-ablation catheter 60a or 60b.

In all configurations the elongated shaft 102 of the diagnostic device 100a or 100b is constructed sufficiently stiff in order to provide a positioning aid for the cryo-ablation catheter 60a or 60b. Distally from the shaft 102 a more flexible outer tubing 112 is used for enabling the formation of a shaped distal portion of the diagnostic device 100a or 100b. Inside the shaped distal portion a shape memory component (not shown, for example Nitinol) might be used for supporting the formation of the desired shape. This shape memory component might extent also proximally from a junction point 102a between the outer tubing 112 and the elongated shaft 102 for ensuring a smooth transition of mechanical properties. This smooth transition can be enhanced by using variable durometers of portions of the elongated shaft 102 and/or of the outer tubing 112. Additionally, the diameter or material properties of the shape memory components might be varied for achieving a smooth transition. At the junction point 102a the elongated shaft 102 and the outer tubing 112 might be connected with each other by means of gluing or welding. Optionally, a shrink tubing (not shown) might be used for supporting the junction point 102a.

A handle 110 is foreseen at the proximal end of the diagnostic devices 100a or 100b for a mechanical manipulation. A kinking protection 111 might be used at the junction between the handle 110 and the elongated shaft 102. At the very proximal end of the handle 110 a connector 114 might be used for connecting cables to recording systems and/or the monitoring unit 42 described above.

In the diagnostic device 100a the distal portion of the outer tubing 112 is shaped such that a U-turn curve 103 is included in the pre-shaped structure between the shaft 102 and the distal loop portion 101. Thus, a distance D of the planes of the distal loop portion 101 and the loop of the cryo-ablation catheter 60a is reduced. Diagnostic electrodes 46i are arranged along the distal loop portion 101 with a variable spacing in azimuthal direction. They are arranged in a pairwise fashion, such that pairs j of respectively two electrodes 46i are formed which are close to each other with a larger spacing between different pairs j. When measuring electrograms this might contribute to an improved signal resolution at the location of each pair j.

When using the electrodes 46i for pacing one pair j of electrodes 46i might be selected for a bi-polar stimulation of the myocardium. As the electrodes 46i are arranged close to each other this might result in a spatially well-defined location of tissue exited by the bi-polar stimulus. When testing if a lesion around a vessel orifice or an annulus blocks the conduction of bio-electric potential from inside the lesion to the tissue outside of the lesion one might attempt to place the respective electrode pair j inside the loop structure of the cry-ablation catheter 60a shown in FIG. 10. Further, locating the electrodes 46i of one pair j close to each other reduces a far field potential and thus contributes to avoiding unintentional stimulation of the tissue outside the lesion. In one embodiment the distance between the electrodes 46i of one pair j might be smaller than 4 mm and more particularly smaller than 2 mm.

When using the electrodes 46i for impedance measurement one pair j might be chosen for forming a three lead configuration (Y-model equivalent circuit) together with one electrode 23i on the loop shaped cryo-applicator tubing 61 of the cryo-ablation catheter 60a show in FIG. 10. In this case one electrode 46i of the pair j might act as the current return path electrode and the other electrode might act as the voltage return path electrode. Here, similar as described for the "two-lead impedance configurations" shown in FIG. 10 the pairs j of electrodes 46i maybe be aligned with electrodes 23i in azimuthal segments along the cryo-applicator loop for creating a three-lead configuration of each segment. In yet another embodiment leads for the electrodes 46i might be wired in parallel for reducing return path impedances similar as described with reference to FIG. 10. For example, one electrode 46i of each pair j might be wired in parallel with one electrode out of all remaining pairs j for creating a common voltage return electrode. In each pair j one electrode can then be used for the current return path and again these electrodes may be wired in parallel for creating a low impedance return path electrode.

Another embodiment for a diagnostic device is the diagnostic device 100b shown in FIG. 11A. The diagnostic device 100b is formed in such a manner that electrodes 46i can be positioned inside a treatment area encircled by the loop shaped cryo-ablation catheter 60a or the balloon shaped cryo-ablation catheter 60b. In other words, the diagnostic device 100b has a tail shape for placing (diagnostic) electrodes 46i inside the ablation area but at the myocardium, while the exit point of the guiding lumen in the cryo-ablation catheter 60a, 60b might be inside the vein. Due to the chosen shape of the diagnostic device 100b the site of contact of these electrodes 46i might be located in proximal direction from the location where diagnostic device 100b exits the inner lumen of the cryo-ablation catheter 60a, 60b. For the depicted embodiment two electrodes 46i are located close to each other in a pairwise fashion. These two electrodes might be located relatively close to each other for local pacing of tissue inside the ablation loop. Again pacing might be applied for confirming that no conduction of bio-electric signals occurs across the lesion produced by ablation. In turn, (bipolar) electrograms might be measured using the electrodes 46i for confirming that no bio-electric signals are conducted from the tissue outside the lesion to the tissue inside the lesion.

It is noted that the depicted diagnostic device 100b can be rotated around its longitudinal axes 115 in order to assess multiple locations along an azimuthal direction.

A second pair of (diagnostic) electrodes 46j might be foreseen at the diagnostic device 100b in a location close to the axis 115. When performing impedance measurements in combination with the cryo-ablation catheters 60a or 60b at least one electrode 46i, 46i of each pair i, j might be used as a current and voltage return electrode in a three lead impedance measurement configuration. For the depicted diagnostic device 100b the pairs i and j are geometrically well separated from each other. This might be of advantage in particular when using a three lead configuration. As only a few electrodes 46i, 46j are needed the diagnostic device 100b can be built up with a diameter of the outer tubing 112 which diameter is smaller than 1.1 mm and more particularly smaller than 0.9 mm.

FIG. 11B shows in an enlarged view a distal end portion 116 of the diagnostic devices 100a and 100b. As can be seen, the distal end portion 116 is shaped in a pig tail or spiral form. This pig tail or spiral form has a double function. One function is that a distal end 116a is encircled by the more proximal parts of the spiral. Thus, when operating the diagnostic devices 100a or 100b inside a cardiac cavity preferably the more proximal parts of the distal end portion 116 will touch the endocardium preventing the distal end 116a from being traumatic. The second function of the depicted shape of the distal end portion 116 can also be seen best from FIG. 11B which illustrates a situation of an ablation catheter with a distal member 62 being located within a steerable sheath 117. Vent holes 118 are foreseen in a distal portion of the sheath 117. When advancing the diagnostic device 100a or 100b inside the inner lumen of an ablation catheter (e.g. the cryo-ablation catheter 60a or 60b shown in FIG. 6) it should not pass across the vent holes 118. The spiral shape of the distal end portion 116 is designed with a sufficiently small curve for avoiding that the distal end 116a can pass across a vent hole 118.

Figure 12:
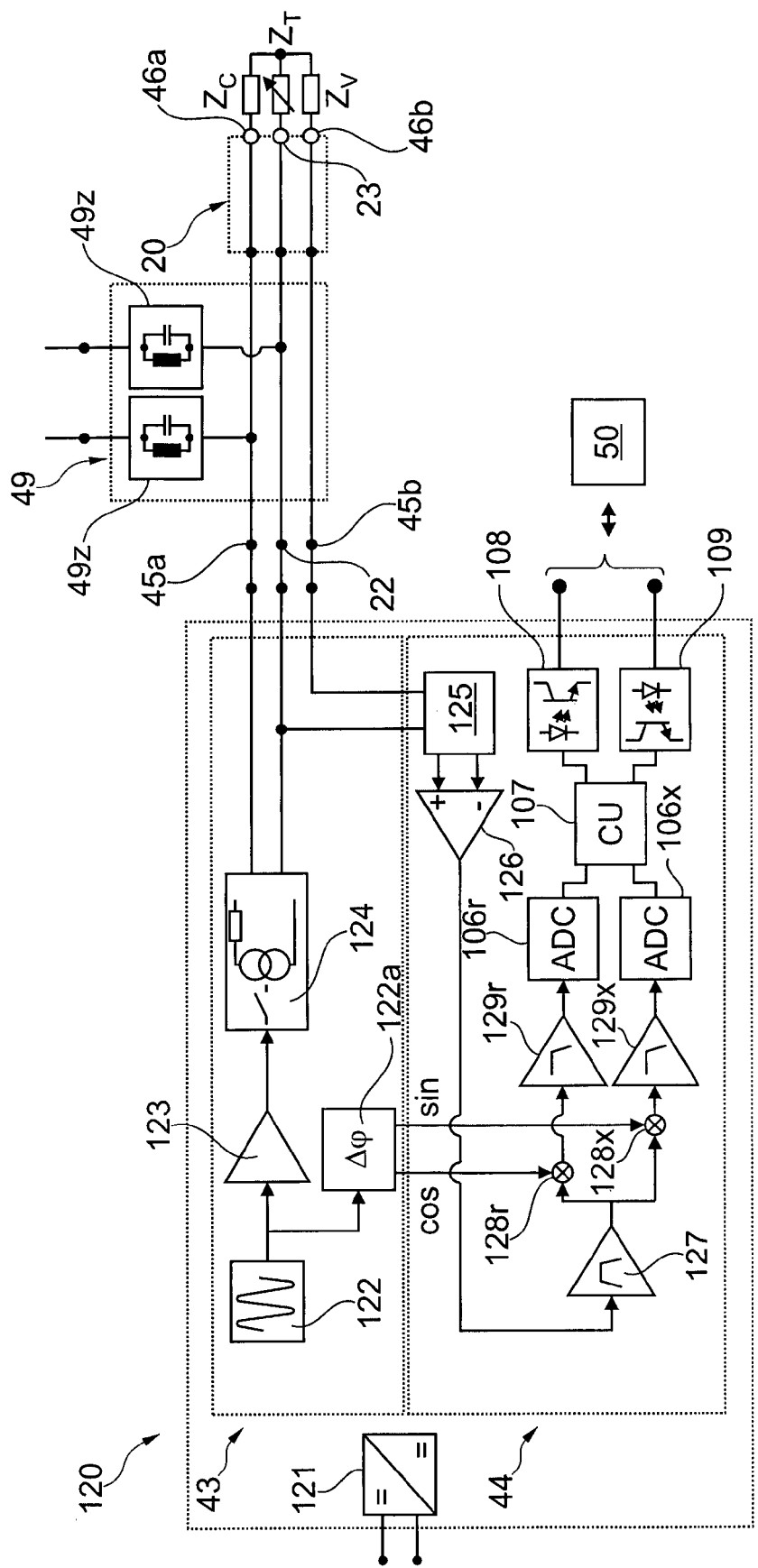
FIG. 12 shows block diagram illustrating an entire ablation system comprising the stimulation unit and the voltage sensor depicted in FIG. 4.

FIG. 12 shows in accordance with an embodiment of the invention a block diagram illustrating an entire ablation system comprising the stimulation unit 43 and the voltage sensor 44 known from FIG. 4.

As has already been mentioned above, applying an active current via a catheter device 20 inside the inside of a human body and in particular inside the heart requires proper measures for ensuring the functional safety of the catheter device 20. Output currents might be limited to an amplitude value of less than 1 mA and more particularly less than 0.15 mA. Output voltage amplitudes might be limited to an amplitude value of less than 5 V and more particularly less than 0.5 V. In the embodiment shown in FIG. 12 the stimulation unit 43 and the voltage sensor 44 are located on one common board 120. Thereby, the monitoring unit 42 shown in FIG. 4 is realized. This monitoring unit is power supplied by a DC/DC converter 121. For limiting stray currents during normal operation as well as during a fault the DC/DC converter 121 provides a high isolation level which can withstand high voltages of at least 5000 V. Its output voltage is in the range between 0.5 V and 20 V. The output might be a single supply or a symmetric supply with a positive and a negative supply rail and a signal ground.

A reference AC signal is generated by a sine generator 122. Precision sinusoid synthesizers as described in the art might be used for providing a sine signal with a low distortion. Typically, the frequency of this reference AC signal is in the range between 5 kHz and 200 kHz. This frequency might be fixed to one value or might be adjustable. In one embodiment two distinct frequencies, one in the low frequency band and one in the high frequency band might be provided. A buffer 123 is foreseen to drive a switchable current source 124 with a sinus voltage input. As will be described in more detail below with reference to FIG. 13, the switchable current source 124 might be adopted for operating at different output current levels for accurately measuring impedances over a range of several orders of magnitude.

The sinusoid output current is passed via leads 22 and 45a to electrodes 23 and 46a via the elongated body of the catheter device 20. As these electrodes 23 and 46a might be used also for other purposes than impedance measurement (e.g. recording of bio-potentials) the filter structures 49z (e.g. band stop filters), which have already been depicted in FIG. 4, might be foreseen for reducing interference of the output AC current with other electronic devices in the operating environment. In the case that two distinct frequencies are used for impedance measurement the filter structure 49z might be a double notch filter. According to the exemplary embodiment described here the filter structure 49z is be located within the split box 49 which has also been already depicted in FIG. 4. For the shown embodiment both electrodes 23 and 46a are connected with the filter structure 49z which might be of particular interest in the case that electrode 46a is located on the catheter device 20 within the body.

The voltage return signal is sensed via electrode 23 and 46b connected to the voltage sensor 44 via lead 22 and return lead 45b. It is noted that the shown embodiment refers to a three lead impedance configuration. At the input of the voltage sensor 44 a protection circuit 125 is foreseen. This protection circuit 125 is used for protecting the common board 120 from high voltages which might be caused e.g. by a defibrillation or RF sources. Appropriate electric protection structures being applicable for the protection circuit 125 are described in the art and may contain diodes and resistors.

The voltage return signal might need amplification to a precisely measurable signal level. For the exemplarily embodiment described here, this amplification is performed in two stages 126 and 127. A differential amplifier 126 performs a first pre-amplification. An amplification stage 127 additionally includes a band pass filter component. This band pass filter is designed such that frequencies outside the operating frequency range of the reference AC signal are damped.

According to basic and well know principles in electronics an impedance Z is composed by a resistance R and a reactance X. The resistance R is the ratio of in-phase voltage to current and reactance X is the ratio of quadrature voltage to current. As is known to a person skilled in the art these two components R and X can be assessed by providing an in-phase signal and a quadrature signal both of defined amplitude. A multiplication unit 128r yields the product of the amplified voltage signal with the in-phase signal and a low pass filter 129r extracts the near DC content of the product which is proportional to the time dependent resistance R(t). Analogously, a signal proportional to the time dependent reactance X(t) is obtained by multiplying the amplified voltage signal with the quadrature signal using multiplication unit 128x and low pass filter 129x.

For accurately assessing the resistance R and the reactance X of the in-phase signal and the quadrature-signal an accurate trimming is needed. This trimming of signal phase is performed by a phase offset sin/cos generator 122a. This sin/cos generator 122a may also be trimmed for compensating phase shifts in other stages (for example the buffer 123 and/or the switchable current source 124) and may be designed for realizing an accurate phase shift at different frequencies.

The corner frequency of low-pass filters 129r and 129x may be chosen identical for both filters. In any case this corner frequency must be sufficiently low in order to reduce signal components of the reference AC signal frequency significantly. Thus, the corner frequency should be smaller than the reference AC signal frequency.

Additionally, the filters 129r and 129x are used as anti-aliasing filters for analog-digital conversion (ADC) of the measured impedance signal by means of ADC converters 106r and 106x. Thus, the corner frequency of the low pass filters 129r and 129x must also be smaller than twice the sampling frequency applied for ADC. The resulting digital data is transferred to a control unit 107.

For maintaining an electrical isolation of the common board 120 two optoelectronic isolators 108 and 109 might be used for enabling a reliable communication between the board 120 and the computing unit 50 which has already been depicted in FIG. 4. The optoelectronic isolator 109 transfers input signals to the control unit 130 using a serial digital protocol. These input signals might be used for selectively starting AD conversion or switching the switchable current source 124 to a defined output level. The optoelectronic isolator 108 transfers output signals to the computing unit 50 using a serial digital protocol. These output signals might result from an AD conversion or the actual output level of the switchable current source 124.

In yet another embodiment the catheter device 20 might use multiple electrodes 23i and/or multiple electrodes 46i as shown in FIG. 6 and FIG. 10. In this case multiplexer circuits might be applied for performing multiple three lead impedance measurements. These multiplexers might be controlled via the optoelectronic isolator 108 and the control unit 107.

For ensuring a functional safety the output currents and output voltage of the switchable current source should not exceed certain limits. Prior to starting an ablation procedure or after terminating an ablation procedure the tissue is at or close to body temperature and impedance is relatively low as can be seen from FIG. 1. These low impedances might be measured for assessing wall contact or lesion formation as described e.g. in U.S. Pat. Nos. 5,673,704 and 6,423,057. During an ablation procedure the impedance might increase by several orders of magnitude due to a progressing ice formation as can be seen from FIGS. 1 and 3. This increase during freezing is indicated by an arrow in the symbol of impedance $Z_T$ (see FIG. 4). However, the application of a constant current to an increasing impedance goes along with an increased voltage level. This might involve safety issues. Additionally, this might cause a significant distortion of the sinusoidal current if the output voltage is close to output rail voltages of the DC/DC converter 121. Here, proper means might be of advantage for reducing the output current supplied by the current source 124 and, thus, limiting also output voltage.

Figure 13:
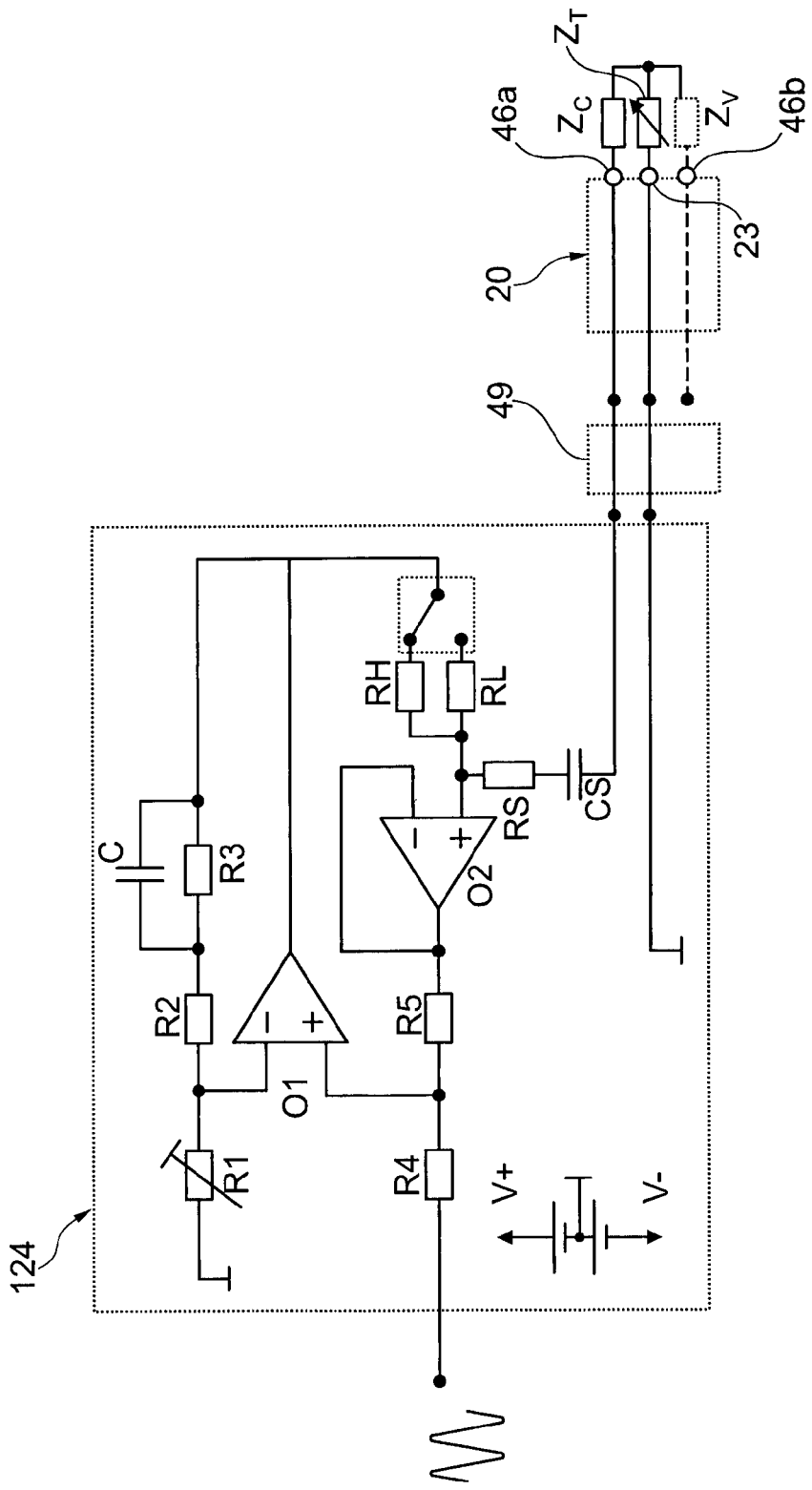
FIG. 13 shows switchable current source for the stimulation unit illustrated in FIG. 12.

FIG. 13 depicts the switchable current source 124 providing two distinct current output levels H (high) and L (low). A person skilled in the art will readily recognize that an operational amplifier O1 in combination with resistors R1, R2, R3, R4 and R5 forms the core of a so called Howland current pump circuit. A symmetric power supply V+ and V− is provided by the DC/DC converter 121 shown in FIG. 12. A sinusoid input voltage is provided at an input pin 11. This might be the output of the buffer 123 or sine generator 122, which are also shown in FIG. 12. The Resistor R1 may be a trimable, i.e. the resistivity of R1 may be adjustable. This allows for adjusting a high output impedance of the Howland current source respectively the switchable current source 124.

As it is described in the art Howland pump circuits need accurate resistors for obtaining accurate output currents of constant levels. Thus, resistors R1 to R5 may be adapted to provide tolerances smaller than 0.5% and more particularly smaller than 0.05%. A capacitor C is foreseen for a defined limitation of the bandwidth of the circuit and for reducing high frequency noise. A switch S in combination with resistors RH and RL is used for selectively switching the output current to a high level (switch S in contact with the resistor RH) or a low level (switch S in contact with the resistor RL). An operation amplifier O2 is wired as a unit gain follower in the feedback loop of the Howland circuit for enabling the use of the switched resistors RH and RL.

For a relatively low impedance expected prior to ablation or after termination of ablation a high current level might be of advantage. Thus, the resistor RH defines the maximum output current of the switchable current source 124 for normal operation. It is chosen such that this current level is still sufficiently small for ensuring functional safety of the catheter device 20. As can be seen from FIG. 1 and FIG. 3, the impedance value might significantly increase during freezing. Thus, the resistor RL is foreseen to switch the catheter device 20 to a low output current level. This lower level may be several orders of magnitude smaller than the high output current level. Additionally, for ensuring a functional safety of the catheter device 20 the voltages V+ and V− might be selected sufficiently small for ensuring that the output voltage at the catheter electrodes 46a, 23, 46b remains below proper limits during normal operation and certain fault conditions.

For further improving the functional safety of the catheter device 20 a resistor RS and a capacitor CS are foreseen in series to the output terminal. This resistor RS further limits output currents and output voltages during normal operation and in certain fault conditions. Furthermore, the resistor RS may contribute for protecting the board 120 (depicted in FIG. 12) from defibrillation pluses and radio frequency energy applied to the body of a patient. Resistor RS may be designed for withstanding high voltage and high power levels.

The capacitor CS is designed such that its reactance is almost negligible (more than one order of magnitude smaller than RS) at the operating frequency of the circuit. In the DC or near DC frequency band however the capacitor CS blocks a current flow from the current source 124 to the body or vice versa. The capacitor CS is designed to withstand high power and high voltage levels and contributes to the functional safety of the switchable current source 124 for normal operation or certain fault conditions. The protecting circuit formed by RS and CS is connected in series with the tip-to-body impedance $Z_T$ to be measured and the circuit the sum of $Z_T$ and the impedance of the protection circuit will be measured. However, as RS and CS are well known quantities the computing unit 50 can correct this when computing the tip-to-body impedance $Z_T$.

In one embodiment the switchable current source 124 might be switched to a high current level while no cryo-ablation ablation is performed. Thus, small impedances can be measured at temperatures close to body temperature for assessing wall contact or tissue necrosis. During freezing the switchable current source 124 may be switched to a low current level for properly measuring high impedance due to ice formation in the tissue. Alternatively, the output voltage of the switchable current source 124 might be monitored for switching the switchable current source 124. If the output voltage level is increased above a certain threshold due to a high body impedance value the output current of the switchable current source 124 is switched to a lower level. If in turn the output voltage level (or the value of the tip-to-body impedance $Z_T$) drops below a certain threshold the output current of the switchable current source 124 might be switched to a high level. Apparently, more than two output current levels might be foreseen for enabling measurement in a range over several orders of magnitude.

In yet another embodiment instead of discrete switching of output current level steps a continuous adaption of the output current provided by the switchable current source 124 may be foreseen. This might be implemented by continuously varying the amplitude of the input sinus voltage on pin 11.

In yet another embodiment discrete level of output currents may be implemented by designing a plurality of current sources and switching individual sources on and off.

At this point it is noted that the voltage return path via electrode 46b is shown in a hatched fashion. This indicates that the switchable current source 124 might be operated in a three lead configuration (using electrode 46b) or in a two lead configuration (not using electrode 46b).

Figure 14:
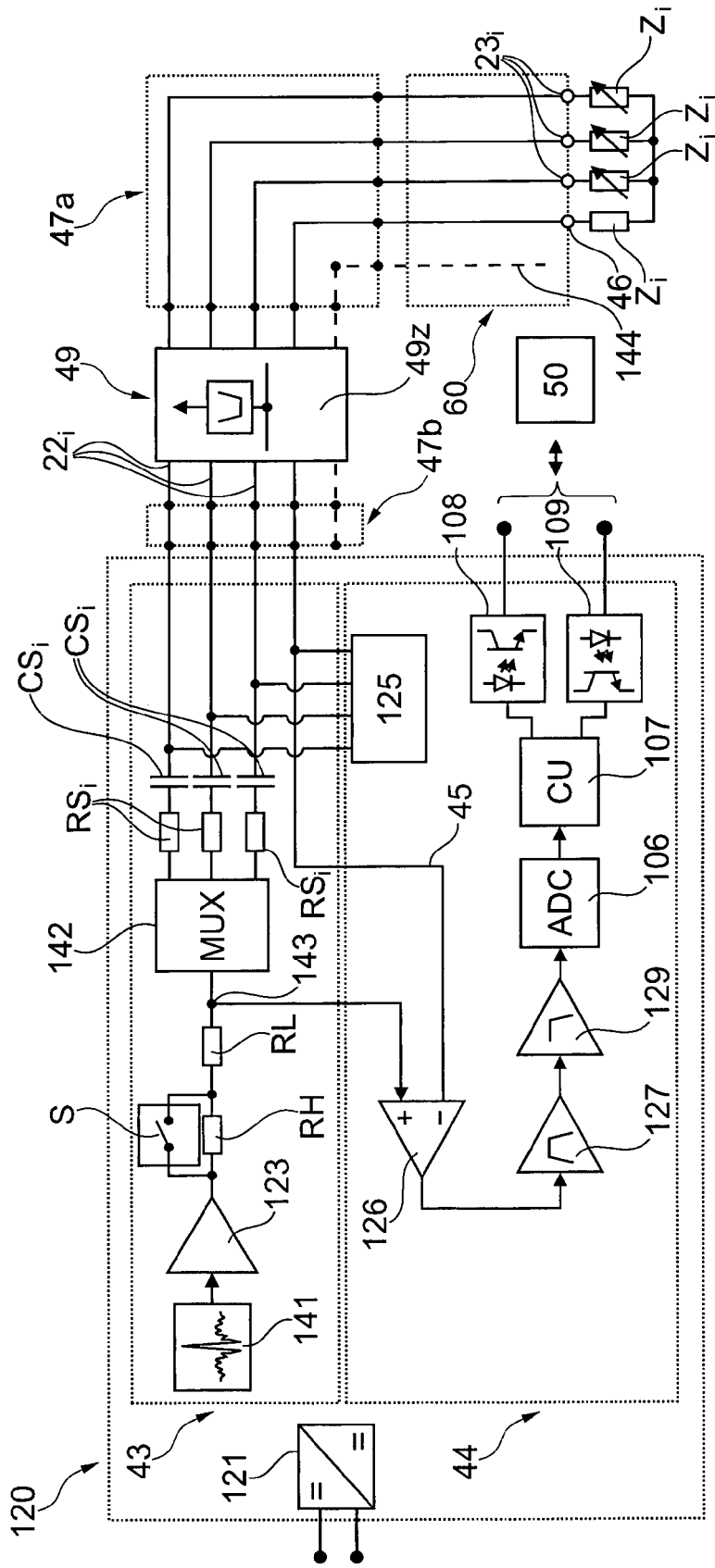
FIG. 14 shows a block diagram of an entire ablation system for measuring multiple two-lead impedances.

FIG. 14 shows in a block diagram an exemplary embodiment for an entire ablation system for measuring multiple two-lead impedances $Z_i$ for an elongated cryo-ablation catheter 60 as depicted in FIG. 6 with cryo-ablation catheters 60a and 60b. Similar as in FIG. 12, an electrically isolated board 120 (realizing the monitoring unit 42) is foreseen for meeting safety requirements. In the shown embodiment the stimulation unit 43 comprises a voltage divider structure. A signal generator 141, which is realized by means of a commercially available synthesizer, provides a voltage signal which is directed via a buffer 123 to resistors RH and RL. Also this configuration is designed for operating at two output levels. By closing the switch S the resistor RH is short-cut and the output voltage level and the output current level is higher compared to the open state of switch S. The high output current level again might be used for measuring relatively low impedance values which are typically expected when tissue under treatment is not frozen (for example prior to or at an initial freezing or after thawing). The stimulation unit 43 is designed such that maximal output current and output voltage at the catheter electrodes 23i is not exceeded when closing the switch S. When opening the switch S the output voltage and current level is decreased for measuring high impedance values which are expected during ice-formation within the tissue under treatment. A node 143 is the branching point of the voltage divider structure directing the signal to the voltage sensor 44 via a differential amplifier 126 and to a multiplexer 142.

The multiplexer 142 is adopted for sequentially measuring multiple impedances $Z_i$ for with the respective electrodes 23i located on the cryo-ablation catheter 60 (see FIGS. 6, 10) via multiple outputs of the multiplexer 142. In the depicted embodiment three outputs are exemplarily shown.

However, also two or more than three outputs may be used. Similar as for the configuration shown in FIG. 13, resistors $RS_i$ and capacitors $CS_i$ are foreseen for each output of the multiplexer 142 for meeting functional safety requirements.

Additionally, leads 22i and a return lead 45 are wired to a protection circuit 125 in order to protect the common board 120 from high energy pulses (for example defibrillation or stimulation pulses). Furthermore, the leads 22i and the return lead 45 are guided via cables 47b, 47a and the split-box 49 to the catheter 60. In the split box band-stop filters 49z might be foreseen to block signals generated by the stimulation unit 43 if the catheter might be used in combination with other devices in a hospital environment. Finally, leads 22i are guided along a longitudinal catheter shaft (not shown) to electrodes 23i located on a cryo-applicator structure of the cryo-ablation catheter 60. In the depicted embodiment the return lead 45 is also guided along the cryo-ablation catheter 60. However, the return lead 45 might be also located on another elongated catheter body as for the diagnostic device 100 shown in FIG. 10 or FIG. 11 or at the surface of the body under treatment. As indicated in FIG. 14 by the hashed line also other leads 144 might be guided to the cryo-ablation catheter 60 for example for enabling temperature or pressure measurements in the cryo-ablation catheter 60.

The multiple impedances $Z_i$ might be measured in a sequential manner using the multiplexer 142. If these impedances $Z_i$ should be determined in a certain frequency band, this could be achieved by using a proper signal shape provided by synthesizer 141. A person skilled in the art will readily understand that by modulating the amplitude of a sine or cosine function with a truncated sinc-function an excitation pulse of finite duration can be created which essentially contains all frequency components within a defined frequency band. Thereby, the basic principles of Fourier Transformation are relied upon. The icon shown within the synthesizer 141 indicates the shape of such a pulse.

The control unit 107 might be adopted for sequentially triggering such pulses and for operating the multiplexer 142 such that the first pulse is transmitted to first lead 22i, the second pulse to the second lead 22i and so on. This sequence can be repeated after the last pulse.

The differential amplifier 126 will then sequentially amplify the pulse response for all impedance values $Z$. These pulse responses might be further amplified and bandpass filtered by the amplification stage 127. Furthermore, an additional anti-aliasing filter 129 might be foreseen. The analog to digital converter 106 transforms the pulse response to discrete digital samples.

In the described configuration the sampling frequency might be higher compared to the embodiment elucidated with reference to FIG. 12 as it might be selected to be at least twice the highest frequency of the excitation pulse. Similar as in FIG. 12 the control unit 107 might be adopted for transmitting the digital measured data via optoelectronic isolators 108 and 109 to the computing unit 50 as described already with reference to FIG. 4. This computing unit 50 might compute the impedance $Z_i$ for the investigated frequency band applying signal analysis methods described in the art (e.g. Fourier analysis, auto-regressive parameter analysis etc.) for each pulse. Thus, sequentially with each pulse the corresponding impedance $Z_i$ is computed for each electrode 23i. From this analysis an impedance value parameter can be computed and displayed for each electrode 23i. Due to the analog signal processing on the common board 120 the measured input voltage might display a known time delay relative to the pulse triggered by the signal generator 141. This, might be corrected when calculating the spectral analysis.

The embodiment shown in FIG. 14 might be used as follows for guiding an ablation treatment. At a starting point of an impedance analysis the cryo-ablation catheter 60 might be introduced into the heart of a patient. In a first step the determined impedance values might be used for assessing a wall contact between the tip of the cryo-ablation catheter 60 and the tissue under treatment. Here, tissue and blood might be at or close to the body temperature of the patient. Consequently, the stimulation unit 43 might be switched to a high output level. As has already been described above, methods for assessing wall contact of a single electrode are described e.g. in U.S. Pat. No. 5,673,704. For the shown embodiment, the wall contact can be assessed for a plurality of electrodes 23$i$ by assessing in a first step sequentially individual impedance values, one impedance value $Z_i$ for each electrode 23$i$ in a configuration where electrodes 23$i$ are located at a certain distance from the wall respectively the tissue (baseline measurement). In other words, during baseline measurements the surface of the electrodes 23$i$ is essentially in contact with the blood stream. Sequential measurement of all impedance values $Z_i$ might take less than 10 seconds and more particularly less than 1 second.

In a second step the cryo-applicator portion (e.g. the cryo-applicator tubing 61 depicted in FIG. 10) of the cryo-ablation catheter 60 is moved towards or pressed against the tissue under treatment. If an electrode 23$i$ is in contact with the wall its surface is essentially in contact with tissue (lower conductivity compared to blood) and the impedance value $Z_i$ being assigned to the respective electrode 23$i$ might increase. As mentioned above, the variation of an impedance value being measured with a single electrode might be used as an indicator for the wall contact.

Applying the embodiment shown in FIG. 14 for a sequential measurement of the impedance values measured with all electrodes 23$i$, in this second step the wall contact can be assessed separately for all electrodes 23$i$. If one or some of the electrodes 23$i$ are not in contact with the wall the procedure (placement and sequential measurement) might be repeated until for most or all electrodes 23$i$ a proper wall contact to the tissue under treatment is confirmed. As the wall contact is related to a relative small increase of the respective impedance value, the stimulation unit 43 might remain switched to a high output level also during confirmation of wall contact.

Once the wall contact is confirmed for a plurality of electrodes 23$i$, a freezing procedure might be started. Thus, ice formation might occur and the impedance values might increase significantly as can be seen from FIGS. 1 and 3. This significant variation of impedance during progressing ice formation is indicated by arrow symbols integrated in the icons for impedances $Z_i$ in FIG. 14.

It is noted that the impedance value $Z_C$ in the return path should exhibit no significant increase of impedance during freezing. This might be achieved by locating the (second or return) electrode 46 sufficiently far from the cooled volume. Due to the significant increase of the impedance values Zi during freezing, the stimulation unit 43 might be switched to a low output level during freezing. The switching may be triggered by defined time points (for example start of freezing or defined interval after the start of freezing) or by threshold values for the output voltage/current provided by the stimulating unit 43).

During freezing the impedance values might be measured for repeated cycles whereas within each cycle impedance values for all electrodes 23$i$ are measured sequentially. For each cycle an impedance value might be calculated for each electrode 23$i$ and displayed for the user for indicating a progress of the ice formation at each single electrode 23$i$. The user might continue freezing until for all electrodes 23$i$ a certain progress is obtained. In another situation one or a few of the electrodes 23$i$ might not display a sufficiently high increase of the respective impedance value. In such a situation the user might perform another placement of the cryo-ablation catheter 60 after a termination of the freezing and might repeat freezing with a modified position of the cryo-ablation catheter 60.

A spatial placement of the cryo-ablation catheter 60 might be performed in combination with clinical imaging modalities such as X-ray, ultrasound or magnetic resonance imaging. For identifying individual electrodes 23$i$ on the images obtained by these modalities proper markers might be applied on the cryo-ablation catheter 60.

After a termination of freezing (in other words after termination of refrigerant supply) rewarming and thawing of the ice layer will occur. Also this process can be monitored by displaying impedance values being assigned to respective electrodes 23$i$. This information might be of value for the user as any attempt of a displacement of the cryo-ablation catheter 60 might potentially cause harm to the tissue under treatment as long as the cryo-ablation catheter 60 remains frozen to the tissue. Thus, in one application a warning might be generated when at least the impedance value being assigned to one single electrode 23$i$ is above a certain threshold. This might prevent a spatial manipulation of the cryo-ablation catheter 60 prior to complete thawing at the contact interface between (a) the cryo-applicator tubing 61 of the cryo-applicator 60 and (b) the tissue under treatment.

When impedance values are sufficiently low after a termination of the freezing the stimulation unit 43 might be switched back to a high output current level respectively output voltage level. Similar as for starting freezing the time points or threshold values might be used to trigger a corresponding switching.

Figure 15B:
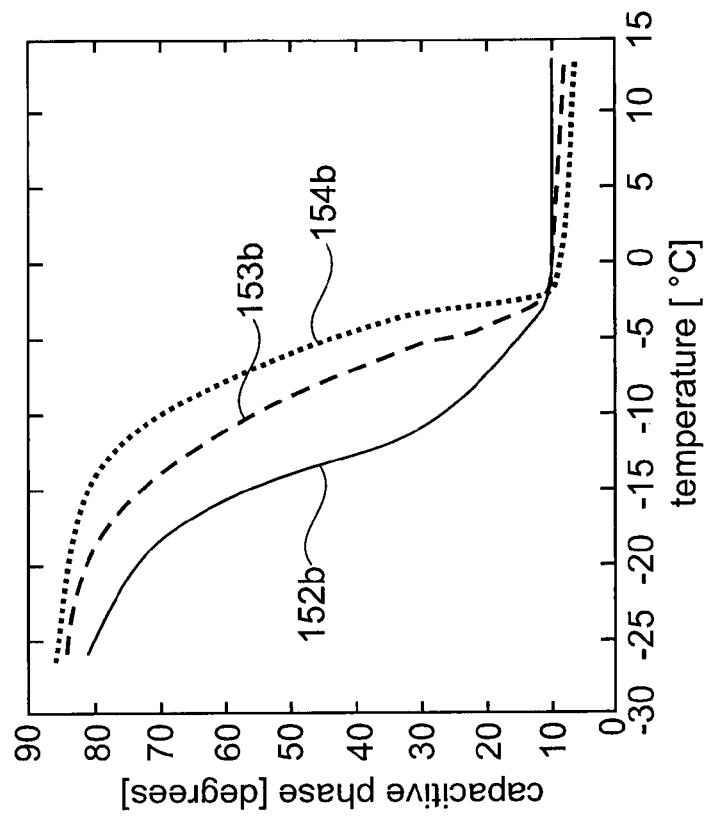
FIG. 15B shows for three operating frequencies the capacitive phase as a function of temperature.
Figure 15A:
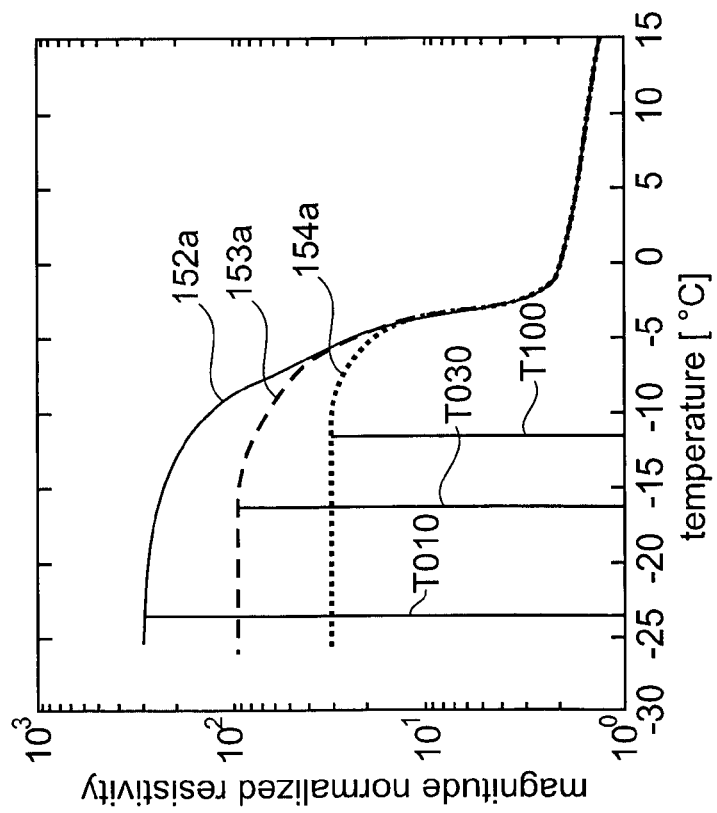
FIG. 15A shows for three operating frequencies the electrical conductivity of muscle tissue as a function of temperature.

FIGS. 15A and 15B present data which may be used for selecting a desired or appropriate operating frequency of the impedance measurement system. In FIG. 15A resistivity measurement curves analogues to those shown in FIG. 1 are presented. By contrast to the experimental situation yielding the electrical conductivity shown in FIG. 1, now the data were obtained at higher frequencies. Data is presented by curves 152$a$, 153$a$ and 154$a$ fitted to the measurements at 10 kHz, 30 kHz and 100 kHz, respectively. As can be seen above the freezing point and slightly below the freezing point the resistivity traces 152$a$, 154$a$ and 154$a$ are comparable to the data shown in FIG. 1 for all three frequencies. However, when decreasing the temperature the resistivity magnitude does not exceed a frequency dependent plateau value. Each of the three resistivity traces 152$a$, 154$a$ and 154$a$ displays an essentially constant value at low temperatures. The vertical line T010 indicates a temperature below which resistivity is essentially constant at 10 kHz. At 30 kHz the corresponding temperature is T030 and at 100 kHz the corresponding temperature is T100. It is noted that the temperatures T010, T030 and T100 increase with increasing frequency.

In FIG. 15B phase angles are shown for 10 kHz (see reference numeral 152$b$), 30 kHz (see reference numeral 153$b$) and 100 kHz (see reference numeral 154$b$). According to the exemplary embodiment described here the phase angle is given by the tan of the ratio between an imaginary part and a real part of the detected electric quantity. Thereby, the phase angle is defined such that capacitive conduction in tissue yields a positive phase angle. The phase continuously increases with decreasing temperature. This transition to essentially capacitive conduction is frequency dependent and occurs at lower temperatures for lower frequencies.

When aiming to continuously monitor the formation of a growing ice layer during freezing (or melting of an ice layer after termination of a freeze) it might be of advantage to select the frequency such that the resistivity is allowed to increase to high values and that a continuous increase is observed during cooling to low temperatures. Furthermore, a smooth continuous transition of the phase angle from small angles to angles near 90° is of advantage during cooling for monitoring ice formation or melting. Thus, the operating frequency should not be chosen too high for monitoring ice formation or melting.

On the other hand also the choice of a too low operating frequency might have negative effects. Biological signals such as intra-cardiac electrograms contain frequency components of a few kilo-Hertz. Thus, recording systems used for diagnostic support of the treatment measure signals with a bandwidth of a few kilo-Hertz. Thus, a low operating frequency for impedance measurement might interfere with such recording systems. Furthermore, unintended stimulation of muscle cells or nerves might occur when applying stimulation currents inside the natural bandwidth of bioelectric function. Based on these considerations an operating frequency between 6 kHz and 24 kHz and more particularly between 10 kHz and 18 kHz may be selected for monitoring of ice formation and melting.

Figure 16:
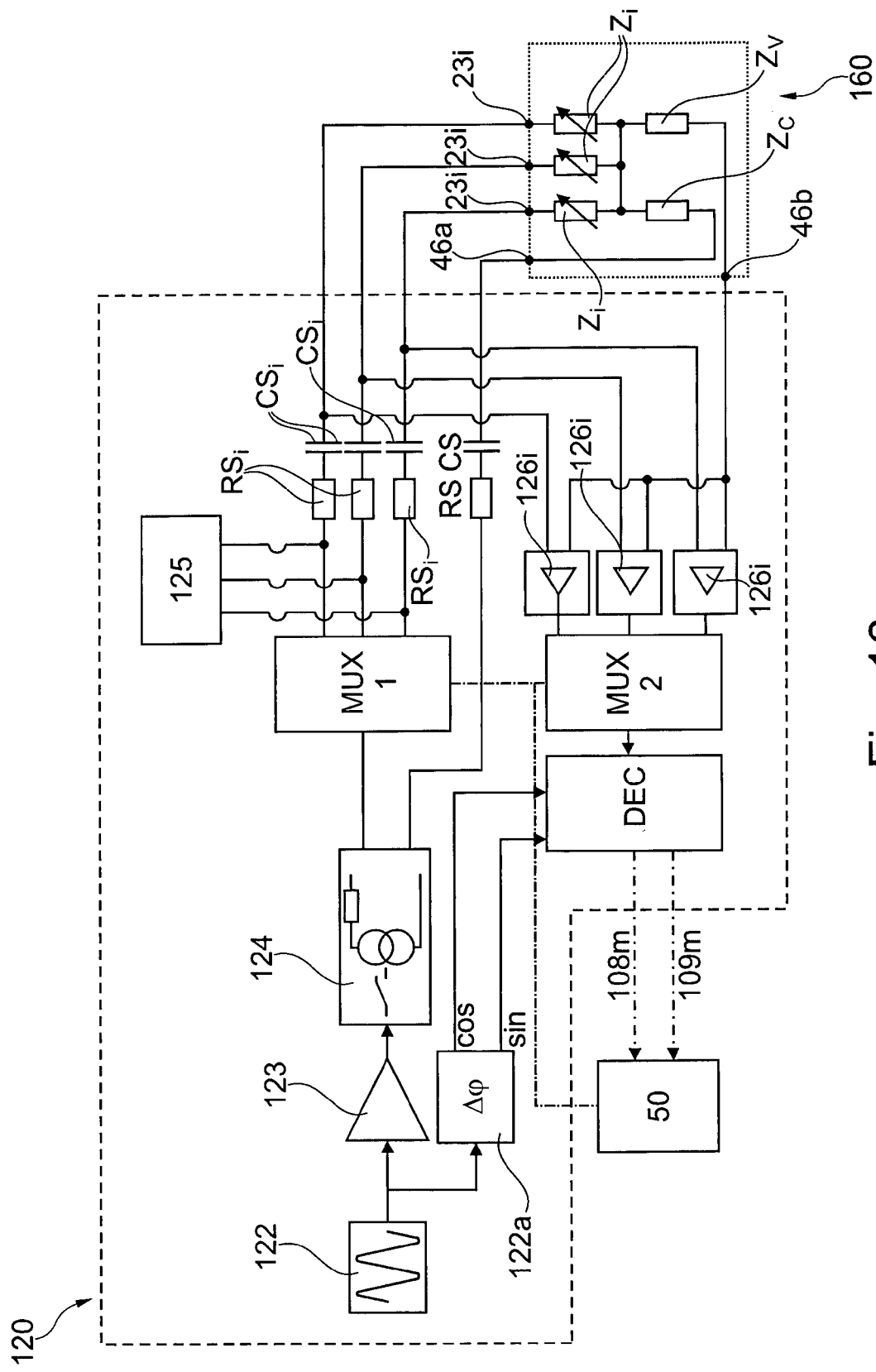
FIG. 16 shows a block diagram of an entire ablation system for performing a three-lead impedance measurement.

FIG. 16 shows a circuit 120 which can be used for performing a three lead impedance measurement at multiple electrodes 23$i$ along a circumference of an ablation catheter inside a body 160. A stimulation current return is realized via electrode 46$a$ and a voltage measurement return is realized via electrode 46$b$. A switchable current source 124 is adapted to provide stimulation current of constant operating frequency at (at least) two essentially constant stimulation levels. At each stimulation level the amplitude of the current is kept essentially constant. Here, for measuring tissue contact a first high level current may be applied. However, for ensuring electrical safety the peak amplitude of this first high level current is kept below 0.1 mA. At a second ablation monitoring level the peak amplitude of this second low level current is below 0.01 mA.

A multiplexer MUX 1 is foreseen for sequentially activating impedance measurement at electrodes 23$i$ along a geometrical dimension of an ablation area. This geometrical dimension may be a circumference for catheter embodiments shown in FIG. 6 or it might be a straight or curved line defined by a longitudinal ablation applicator. For ensuring electrical safety also in fault conditions a voltage limiter unit 125 is foreseen. This voltage limiter unit 125 limits the voltage at each output of the multiplexer to a maximal absolute peak voltage. For example, voltage may be limited to the range −1 V to +1 V. RC structures (Ri, Ci and return structure Rr, Cr) are foreseen to limit the current in fault condition to a maximal amplitude of 0.4 mA at operating frequency and to a maximal amplitude of 0.04 mA at near DC frequencies. It is noted that the RC circuit in combination with the voltage limiter provides also a protection of the circuit from external electric sources such as radio frequency ablation currents or defibrillation pulses.

As outlined above, an unintended stimulation of tissue by the measurement current has to be avoided. Upon electrical activation of biological tissue (muscle cells or nerve) the voltage across the cell membrane displays a step-like response with the typical amplitude around 0.1 V. Thus, stimulation of tissue may be avoided if the peak value of the output voltage applied between the extra-cellular stimulation electrodes 23$i$ and 46$a$ is kept below the half of this value, i.e. 0.05 V. It is noted that these limits also reduce interference with other recording systems in clinical use. Thus, by limiting voltage between electrodes in tissue contact no stimulation may occur even if the circuit is operated at relatively low operating frequency below 24 kHz or more particularly below 18 kHz. On the other hand, for achieving a desired accuracy for impedance measurement the output voltage should not be selected to small. Thus the circuit may be designed to operate with output voltages in the range of 0.002 V to 0.05 V. For the depicted circuit this voltage limitation is achieved as follows:

During monitoring of wall contact (operation at a first high current level) the magnitude of the tissue impedance is relatively low. Thus, the RC circuits are designed in such a way that the magnitude of their impedance is relatively high. In other words, the RC circuits in combination with the voltage limiter unit 125 and the tissue impedance form a voltage divider structure. This structure is designed such that output voltage between stimulation electrodes remains in the interval described above for tissue contact monitoring.

During ablation procedure the impedance between electrodes (Zi+Zc) may significantly increase due to an ice formation in tissue. Thus, the RC circuits in combination with the voltage limiter structure 125 cannot provide a sufficient limitation of the voltage during ablation. Therefore, the stimulation current is reduced by switchable current source 125 during ablation for limiting the voltage between the stimulation electrodes to the desired interval.

It is noted that the operation of the multiplexer MUX 1 is the same for monitoring of wall contact and ablation. All electrodes 23$i$ are sequentially stimulated in a cyclic fashion. Multiple input amplifiers units 126$i$ are foreseen for individually amplifying the voltage at each impedance Zi. Each amplifier unit 126$i$ contains an input protection unit, an amplifier and a band pass filter. These components are analogues to those depicted in FIG. 12 with the reference symbols 125, 126 and 127. A second multiplexer MUX 2 is used to selectively pass the amplified signals to further processing. A control unit 50 operates both multiplexers essentially simultaneously such that when a particular electrode 23$i$ is stimulated the voltage at the same electrode 23$i$ is passed through the second multiplexer MUX 2. The output of multiplexer MUX 2 is guided to a decoder unit DEC. Analogously, as described in FIG. 12, inside this decoder unit DEC two multipliers 128$r$/128$x$ and two low pass filters 129$r$/129$x$ are driven by a Cosine and a Sine signal for splitting the input signal into a real part impedance output 108$m$ and an imaginary part impedance output 109$m$.

Due to the multiplexing at the outputs 108$m$ and 109$m$ of the decoder unit DEC proper measures have to be taken for obtaining reliable impedance measurements. A settling time has to be considered when multiplexing the impedance measurements at electrodes 46$i$. Measurements are only valid when waiting the settling time before taking measurement. This can be achieved only if the following frequencies are carefully selected.

First, a cycle rate must be defined. In order to provide the operator with a continuous monitoring of wall contact or ablation progress, measurements at all electrodes 23$i$ have to be performed in a cyclic fashion. Within one frame cycle one measurement is performed with each electrode. This cycle rate is preferable in the interval of 2 Hz to 20 Hz.

A multiplexer switching frequency is defined by the product of the cycle rate and number of stimulation electrodes 23$i$. This multiplexer switching frequency is preferably in the range of 100 Hz and 1000 Hz.

The current source operation frequency may be chosen as described in FIG. 15. This current source frequency must be considered when designing the low pass filters inside the decoder DEC. The corner frequency of the low pass must be smaller than the current source operation frequency. However, for achieving a sufficiently short settling time the corner frequency must be larger than the multiplexer frequency. Therefore, the corner frequency of the low pass must be larger than the multiplexer switching frequency but smaller than the current source operation frequency.

During ablation the capacitive impedance (i.e. the signal at output 109*m*) will increase faster with progressing ice formation compared to the real part impedance (i.e. the signal at output 108*m*). Thus, the relation of capacitive and real part impedance might be used as a marker for progress of ice formation. For example for creating a lesion of sufficient spatial extension freezing might be continued until the capacitive impedance is large or equal than the real part impedance.

A proper impedance parameter as described above may be defined by using the capacitive impedance. Information may be presented to the user by multiple bars on the display. Each bar corresponds to the measurement obtained at a particular stimulation electrode 23*i*. The length of each bar might be defined by a properly chosen impedance parameter such as the logarithm of the absolute impedance of the recording at the respective electrode 23*i*. The color of each bar may be defined by the ratio between the imaginary and the real part of the local measurement. For instance if the imaginary part is larger than the real part, a particular color might be chosen for the bar. If the imaginary is smaller than the real part a second color is assumed to each bar. This might provide an efficient matter to display phase information to the user. However, the ratio for color change may be variable or user selectable. Furthermore, the color might be adapted in multiple steps with properly selected thresholds.

It should be noted that the term "comprising" does not exclude other elements or steps and the use of articles "a" or "an" does not exclude a plurality. Also elements described in association with different embodiments may be combined. It should also be noted that reference signs in the claims should not be construed as limiting the scope of the claims.

LIST OF REFERENCE SIGNS

11 temperature dependent normalized resistivity for NaCl solution
12 temperature dependent normalized resistivity for muscle tissue
18 temperature profile within tissue under treatment
20 cryo-ablation catheter/catheter device
21 cryo portion/catheter tip
21*a* embodiment of catheter tip
21*b* embodiment of catheter tip
22 lead
22*a* lead/first lead
22*b* lead
22*i* leads
22*k* leads (not directly visible)
23 first electrode
23*a* tip portion/first electrode
23*c* protruding portion
23*d* (elongated) distal member
23*i* plurality of electrodes
23*j* electrode of an electrode pair
24 blood pool/blood flow
25 tissue under treatment
26 fluid supply line/first fluid line
26*a* fluid return line/second fluid line
27 boiling chamber
27*a* inner boiling chamber
27*b* outer boiling chamber
28 thickness of frozen tissue region
29 frozen tissue region
29*a* border zone
29*b* extended border zone
31 tip-to-body impedance as a function of the thickness of the ice-layer
32 tip-to-body impedance with first electrode 23*a* and cryo-applicator 53 electrically connected in parallel
35 normalized voltage indicating the tip-to-body impedance 31
36 normalized voltage indicating the tip-to-body impedance 32 with first electrode 23*a* and cryo-applicator 53 electrically connected in parallel
40 cryo-ablation console
41 ablation control unit
42 monitoring unit
43 stimulation unit
44 voltage sensor
45 return lead
45*a* return lead
45*b* return lead
46 second electrode
46*a* electrode
46*b* electrode
46*i* (diagnostic) electrodes
46*j* electrode of an electrode pair
47*a* connection cable
47*b* connection cable
48 separate cable
49 split box
49*z* filter structure
50 computing unit
52 elongated catheter shaft
53 cryo-applicator
54 support element
55 temperature sensor
55*a* temperature sensor within inner boiling chamber 27*a*
55*b* temperature sensor within outer boiling chamber 27*b*
56 pull wire
57 layer (thermally conducting, electrically insulating)
60 cryo-ablation catheter
60*a* embodiment for cryo-ablation catheter (loop shaped)
60*b* embodiment for cryo-ablation catheter (balloon shaped)
61 cryo-applicator tubing
61*a* active portion
62 distal member
62*b* proximal portion
63 positioning catheter
64 guide wire
65 elongated catheter shaft
66 balloon like applicator structure
70 refrigerant flow rate over time
71 temperature over time
80 refrigerant flow rate over time
81 impedance value over time
90 cryo-ablation catheter
91 exit point
92*i* micro-holes
93 sealing structure
95 support structure
100 diagnostic device
100*a* embodiment of diagnostic device
100*b* embodiment of diagnostic device
101 distal loop portion
102 elongated shaft
102*a* junction point
103 U-turn curve
106*r* ADC converter 106x ADC converter
107 control unit
108 optoelectronic isolator
108m real part impedance output
109 optoelectronic isolator
109m imaginary part impedance output
110 handle
111 kinking portion
112 outer tubing
115 longitudinal axis
116 distal end portion
116a distal end
117 steerable sheath
118 vent holes
120 common board/PCB
121 DC/DC converter
122 sine generator
122a sin/cos generator
123 buffer
124 switchable current source
125 protection circuit/second protection circuit
126 differential amplifier
126i input amplifier units
127 amplification stage
128r multiplication unit
128x multiplication unit
129 anti-aliasing filter
129r low pass filter
129x low pass filter
141 signal generator/synthesizer
142 multiplexer
143 node/branching point
152a/153a/154a normalized resistivity curves
152b/153b/154b capacitive phase curves
160 body
f1/f2/f3 flow rates
p1/p2/p3 impedance values
t0/t1/t2 time points
te end time point
Tt threshold temperature
j segment/pair of electrodes
i pair of electrodes
S switch
$Z_T$ tip-to-body impedance
$Z_C$ impedance
$Z_V$ impedance
O1, O2 operational amplifier
R1, ... 5 Resistors
I1 input pin
C capacitor
RH, RL resistors
RS (safety) resistor/part of first protection circuit
CS (safety) capacitor/part of second protection circuit
$Z_i$ one two-lead impedance from multiple two-lead impedances
$RS_i$ (safety) resistor/part of first protection circuit
$CS_i$ (safety) capacitor/part of second protection circuit
T010/T030/T100 constant temperature values
MUX1/MUX2 multiplexer
DEC decoder unit

The invention claimed is:

1. A catheter device for ablating biological material, comprising a catheter device and a measurement device, the catheter device comprising a longitudinal structure;
an applicator for ablating the biological material, wherein the applicator is installed at the longitudinal structure; a first electrode being attached to the applicator or to the longitudinal structure; a second electrode being attached to the longitudinal structure; an interface being connected directly or indirectly to the longitudinal structure; a first lead electrically connecting the first electrode with the interface; a second lead electrically connecting the second electrode with the interface; wherein the interface is configured for electrically connecting the first lead and the second lead with the measurement device for electrically stimulating the first electrode and the second electrode and for detecting an electric quantity being associated with an electric response of an biological material being located in between the two stimulated electrodes;
the measurement device comprising
a stimulating unit for electrically stimulating the first electrode and the second electrode;
a detecting unit for detecting the electric Quantity received from the two electrodes; and
a computing unit for determining, based on the detected electric Quantity, an electric impedance of the biological material being located in between the two stimulated electrodes;
wherein the stimulating unit is configured for stimulating the first electrode and the second electrode with an adjustable electric amplitude in such a manner that with a first level of the adjustable electric amplitude a wall contact between (i) the first electrode and/or the second electrode on the one hand and (ii) tissue on the other hand is detected and with a second level of the adjustable electric amplitude a formation of ice within the biological material being located in between the top two stimulated electrodes is recognized, and
wherein the second level is below 0.01 mA.

2. The catheter device as set forth in claim 1, wherein the applicator is a cryogenic applicator and wherein the catheter device further comprises
a first fluid line extending between the interface and the cryogenic applicator and being configured for feeding a cooling fluid to the cryogenic applicator; and
a second fluid line extending between the cryogenic applicator and the interface and being configured for discharging the cooling fluid from the cryogenic applicator.

3. The catheter device as set forth in claim 1, wherein the longitudinal structure comprises
a shaft;
a positioning device being movable along an axis of the shaft; and
a distal member being mounted at a distal end of the positioning device.

4. The catheter device as set forth in claim 3, wherein the applicator extends between a distal end of the shaft and a proximal end of the distal member and,
in an operational state allowing for ablating biological material, the applicator adopts either a loop shape or a balloon shape.

5. The catheter device as set forth in claim 1, further comprising
a diagnostic device being insertable and/or shiftable within the longitudinal structure comprising diagnostic electrodes for recording electrical signals being associated with a physiological function of a human or animal body being treated with the catheter device; and
a wiring arrangement electrically connecting the diagnostic electrodes with the interface.

6. The catheter device as set forth in claim 1, wherein the first electrode comprises
   a first portion for contacting the tissue; and
   a second portion being contactable with cryogenic fluid, wherein the second portion comprises a surface contour, which, compared to a surface contour of the first portion, increases the thermal interaction area between the cryogenic fluid and the first electrode.

7. The catheter device as set forth in claim 1, further comprising
   at least one further first electrode;
   a lead arrangement electrically connecting the at least one further first electrode with the interface.

8. The catheter system as set forth in claim 1, wherein the stimulating unit comprises
   a reference signal generator; and
   a voltage and/or current source operable in response to the reference signal generator,
   wherein the voltage and/or current source is connected to the interface of the catheter device.

9. The catheter system as set forth in claim 1, wherein the stimulating unit comprises a switching unit for changing in a discrete manner the strength of stimulating the first electrode and the second electrode.

10. The catheter system as set forth in claim 9, wherein the stimulation unit is configured to change a stimulating quantity for the first electrode and the second electrode from a first level to a second level, wherein the second level is smaller than the first level by at least a factor of 10.

11. The catheter system as set forth in claim 10, wherein the first level is an AC current below 0.15 mA.

12. The catheter system as set forth in claim 1, wherein the stimulating unit comprises
   a multiplexing unit being connected with the interface,
   wherein the multiplexing unit and the interface are configured for stimulating the first electrode and wherein one channel of the multiplexing unit is assigned to one of the electrodes.

13. The catheter system as set forth in claim 1, wherein the measurement device comprises
   means for splitting the detected electric quantity into a real part and into an imaginary part,
   wherein the computing unit is configured for comparing the real part with the imaginary part and for determining, based on the result of comparing, the electric impedance of the biological material.

14. The catheter system as set forth in claim 1, wherein the stimulating unit is configured for stimulating the first electrode and the second electrode at an operating frequency between 6 kHz and 24 kHz.

15. The catheter system as set forth in claim 1, wherein the stimulating unit comprises
   a first protection circuit being assigned to the second electrode and being configured for limiting a current flow to and/or from the second electrode and/or wherein the detecting unit comprises
   a second protection circuit being assigned to the first electrode and to the second electrode and being configured for keeping a voltage level between the first electrode and the second electrode within a predefined range.

16. The catheter system as set forth in claim 1, wherein the detecting unit comprises
   a third protection circuit being connected between the computing unit and other electronic components of the detecting unit and/or wherein the measurement device comprises
   a fourth protection circuit being assigned to a power input of the measurement device and preventing over-voltages and/or over-currents being generated by an external power source from reaching the measurement device.

17. The catheter system as set forth in claim 1, wherein the stimulating unit comprises
   a signal generator which is configured to generate pulses of finite duration containing frequency components between a first frequency value and a second frequency value, wherein the first frequency value is lower than the second frequency value, and
   wherein the signal generator is configured for electrically stimulating the first electrode and the second electrode with the generated pulses.

18. Method for ablating biological material, the method comprising
   (a) ablating the biological material with an applicator of a catheter device of a catheter system comprising the catheter device and a measurement device, wherein the catheter device comprises
      a longitudinal structure;
      an applicator for ablating the biological material, wherein the applicator is installed at the longitudinal structure;
      a first electrode being attached to the applicator or to the longitudinal structure;
      a second electrode being attached to the longitudinal structure;
      an interface being connected directly or indirectly to the longitudinal structure;
      a first lead electrically connecting the first electrode with the interface;
      a second lead electrically connecting the second electrode with the interface;
      wherein the interface is configured for electrically connecting the first lead and the second lead with a measurement device for electrically stimulating the first electrode and the second electrode and for detecting an electric quantity being associated with an electric response of an biological material being located in between the two stimulated electrodes;
   (b) electrically stimulating the first electrode and the second electrode by means of a stimulating unit of the measurement device; and
   (c) detecting, by means of a detecting unit of the measurement device, an electric quantity received from the two electrodes and being associated with an electric response of a biological material being located in between the two stimulated electrodes; and
   (d) determining, by means of a computing unit of the measurement device and based on the detected electric quantity an electric impedance of the biological material being located in between the two stimulated electrodes;
      wherein the stimulating unit is configured for stimulating the first electrode and the second electrode with an adjustable electric amplitude in such a manner that with a first level of the adjustable electric amplitude a wall contact between (i) the first electrode and/or the second electrode on the one hand and (ii) tissue on the other hand is detected and with a second level of the adjustable electric amplitude a formation of ice within the biological material being located in between the two stimulated electrodes is recognized, and
      wherein in the second level is below 0.01 mA.

* * * * *